(12) United States Patent
Dealwis

(10) Patent No.: US 9,889,129 B2
(45) Date of Patent: Feb. 13, 2018

(54) METHOD OF MODULATING RIBONUCLEOTIDE REDUCTASE

(71) Applicant: Case Western Reserve University, Cleveland, OH (US)

(72) Inventor: Chris Dealwis, Highland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 14/387,151

(22) PCT Filed: Mar. 21, 2013

(86) PCT No.: PCT/US2013/033271
§ 371 (c)(1),
(2) Date: Sep. 22, 2014

(87) PCT Pub. No.: WO2013/142669
PCT Pub. Date: Sep. 26, 2013

(65) Prior Publication Data
US 2015/0094314 A1     Apr. 2, 2015

Related U.S. Application Data

(60) Provisional application No. 61/613,694, filed on Mar. 21, 2012.

(51) Int. Cl.
| | |
|---|---|
| *A61K 31/496* | (2006.01) |
| *A61K 31/495* | (2006.01) |
| *A61K 45/06* | (2006.01) |
| *A61K 31/165* | (2006.01) |
| *A61K 31/166* | (2006.01) |
| *A61K 31/4035* | (2006.01) |
| *A61K 31/4152* | (2006.01) |
| *A61K 31/223* | (2006.01) |
| *C07C 237/22* | (2006.01) |
| *C07C 243/28* | (2006.01) |
| *C07D 209/48* | (2006.01) |
| *C07D 295/088* | (2006.01) |

(52) U.S. Cl.
CPC .......... *A61K 31/496* (2013.01); *A61K 31/165* (2013.01); *A61K 31/166* (2013.01); *A61K 31/223* (2013.01); *A61K 31/4035* (2013.01); *A61K 31/4152* (2013.01); *A61K 31/495* (2013.01); *A61K 45/06* (2013.01); *C07C 237/22* (2013.01); *C07C 243/28* (2013.01); *C07D 209/48* (2013.01); *C07D 295/088* (2013.01)

(58) Field of Classification Search
CPC ..................................................... A61K 33/15
USPC ........................................................ 514/639
See application file for complete search history.

(56) References Cited

U.S. PATENT DOCUMENTS

| | | | | |
|---|---|---|---|---|
| 5,610,192 | A | * 3/1997 | Cohen .................. | A61K 31/135 514/614 |
| 6,608,061 | B2 | * 8/2003 | Yonetani .............. | C07C 323/16 514/237.8 |
| 7,619,115 | B2 | 11/2009 | Gericke et al. | |
| 2009/0306022 | A1 | 12/2009 | Nelson et al. | |
| 2011/0245304 | A1 | 10/2011 | Yen et al. | |

FOREIGN PATENT DOCUMENTS

| | | | | |
|---|---|---|---|---|
| WO | WO 9406280 A1 | * 3/1994 | ........... | A61K 31/135 |
| WO | WO 2008134474 A2 | * 11/2008 | ........... | A61K 31/495 |

OTHER PUBLICATIONS

Harfenist, M. et al., (JACS vol. 76 pp. 4991-4993. Published 1954).*
Asis, S.E. et al., II Farmaco vol. 51 pp. 517-523, published 1999.*
Melnyk, P. et al., Bioorganic and Medicinal Chemistry Letters vol. 16 pp. 31-35 published 2006.*
Chaston, T.B. et al., Clinical Cancer Research vol. 9 pp. 402-414. Published 2003.*
Hoyes, K.P. et al., Cancer Research vol. 52 pp. 4591-4599. Published 1992.*
Chaston et al (Clinical Cancer Research vol. 9 pp. 402-414 published 2003).*
Finch et al, (Biochem Pharmacol vol. 59, pp. 983-991, published 2000).*
Melnyk et al (Bioorganic and Medicinal Chemistry Letters vol. 16 pp. 31-35).*
Barker et al (Clinical Cancer Research vol. 12 pp. 2912-2918 published 2006).*
Melnyk et al (Bioorganic and Medicinal Chemistry Letters vol. 16 pp. 31-35, published 2006).*
Fife, R.S., et al. "Effects of doxycycline on cancer cells in vitro and in vivo", Advances in Dental Research, 1998, vol. 12, pp. 94-96.
Shao, J., et al., "Ribonucleotide reductase inhibitors and future drug design" Current cancer drug targets, 2006, vol. 6, pp. 409-431.

* cited by examiner

*Primary Examiner* — Timothy Thomas
*Assistant Examiner* — George W Kosturko
(74) *Attorney, Agent, or Firm* — Tarolli, Sundheim, Covell & Tummino LLP

(57) ABSTRACT

A method of modulating ribonucleotide reductase activity in a neoplastic cell includes administering to the cell an amount of a ribonucleotide reductase allosteric modulator (RRA-mod), the amount being effective to inhibit neoplastic cell growth.

5 Claims, 12 Drawing Sheets

Wavelength (nm)

Figs. 13A-B

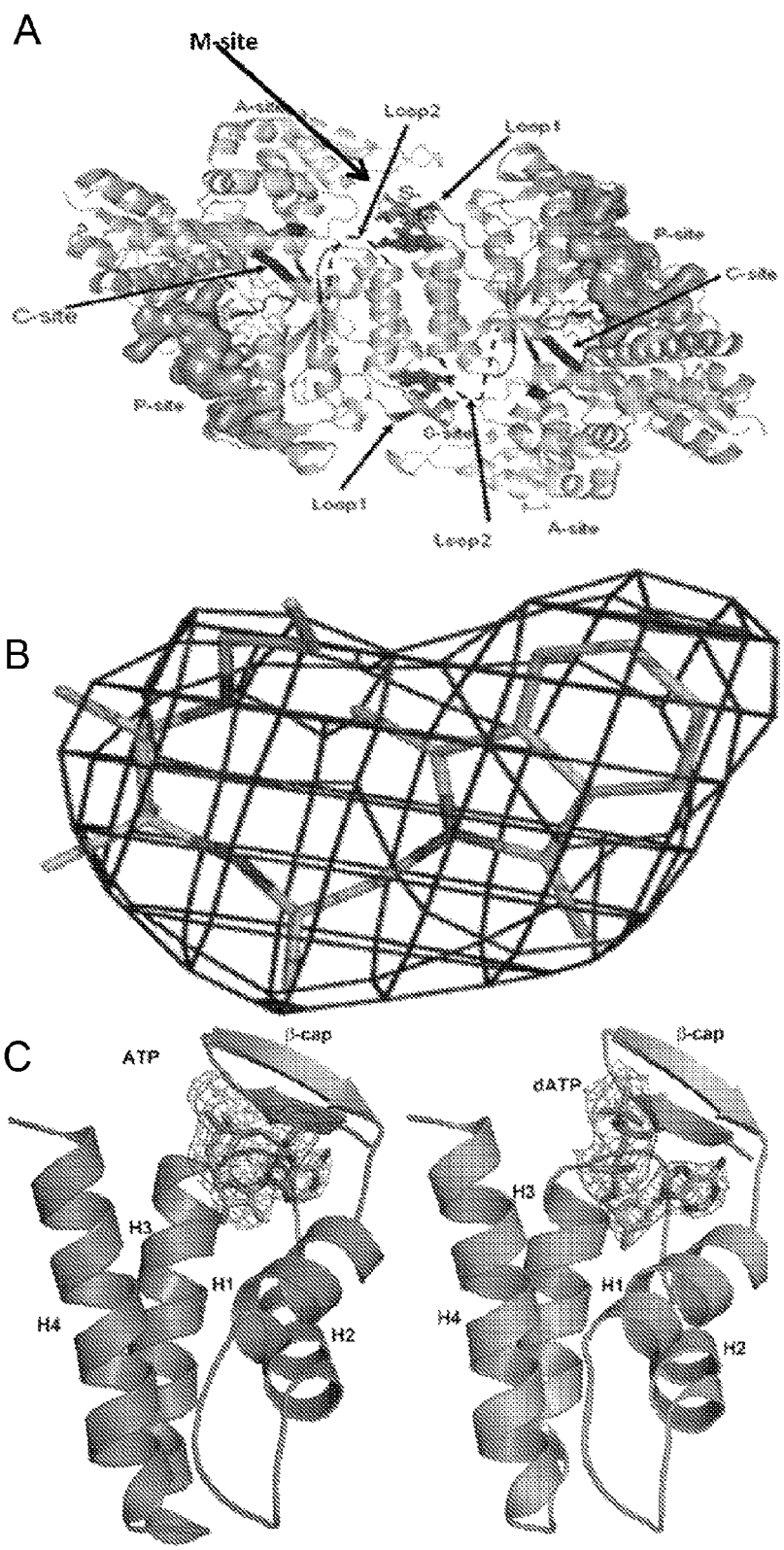
Figs. 16A-C

SEQUENCE LISTING

```
<160> NUMBER OF SEQ ID NOS: 1

<210> SEQ ID NO 1
<211> LENGTH: 21
<212> TYPE: PRT
<213> ORGANISM: Homo sapiens

<400> SEQUENCE: 1

Met His Val Ile Lys Arg Asp Gly Arg Gln Glu Arg Val Met Phe Asp
1               5                   10                  15

Lys Ile Thr Ser Arg
            20
```

METHOD OF MODULATING RIBONUCLEOTIDE REDUCTASE

RELATED APPLICATION

This application claims priority from U.S. Provisional Application No. 61/613,694, filed Mar. 21, 2012, the subject matter of which is incorporated herein by reference in its entirety.

GOVERNMENT FUNDING

This invention was made with government support under Grant No. CA100827 awarded by The National Institutes of Health (NIH). The United States government has certain rights in the invention.

FIELD OF THE INVENTION

The present invention relates to selective modulators of ribonucleotide reductase (RR) and to methods of using such modulators for therapeutic applications.

BACKGROUND

Ribonucleotide reductase (RR) is a highly regulated enzyme which catalyzes the de novo dNTP synthesis pathway that is ubiquitously present in human, bacteria, yeast, and other organisms. RR plays a crucial role in de novo DNA synthesis by reducing ribonucleoside diphosphates to 2'-deoxy ribonucleoside diphosphates and maintains balanced pools of deoxynucleoside triphosphates (dNTPs) in the cell.

RRs are divided into three classes, I to III, based on the method of free-radical generation. All eukaryotic organisms encode a class I RR, consisting of an $\alpha n\beta n$ multi-subunit protein complex, in which the minimally active form is $a2\beta2$. The $\alpha$ or RR1 (large) subunit contains the catalytic (C-site) and two allosteric sites, while the $\beta$ or RR2 subunit houses a stable tyrosyl free radical that is transferred some 35 Å to the catalytic site to initiate radical-based chemistry on the substrate.

RR is regulated transcriptionally, allosterically and, in the yeast S. cerevisiae, RR is further regulated by subunit localization and by its protein inhibitor Sml1. In mammalian cells, RR activity is also controlled by the RR2 levels. Consistent with the varying RR2 levels, dNTP pools also vary with the phases of the cell cycle, reaching the highest concentration during S-phase. RR is regulated by an intricate allosteric mechanism. The two allosteric sites of RR are the specificity site (S-site), which determines substrate preference, and the activity site (A-site), which stimulates or inhibits RR activity depending on whether ATP or dATP is bound.

RR is directly involved in neoplastic tumor growth, metastasis, and drug resistance. The proliferation of cancer cells requires excess dNTPs for DNA synthesis. Therefore, an increase in RR activity is necessary as it helps provide extra dNTPs for DNA replication in primary and metastatic cancer cells. Because of this critical role in DNA synthesis, RR represents an important target for cancer therapy. However, existing chemotherapies that target ribonucleotide reductase are nucleoside-based analogs. Hence they are promiscuous, leading to nonspecific binding of other nucleoside binding proteins which results in unwanted side effects. Therefore, there is a need for compositions and methods for specifically targeting and inhibiting RR activity in neoplastic cells in the treatment of neoplastic disorders.

SUMMARY

Embodiments described herein relate to compounds and methods of modulating ribonucleotide reductase activity in a neoplastic cell. The method includes administering to the cell an amount of a ribonucleotide reductase allosteric modulator (RRAmod). The amount of RRAmod is the amount effective to inhibit neoplastic cell growth.

In another aspect, a method of treating a neoplastic disorder in a subject is provided. The method includes administering to neoplastic cells of the subject a therapeutically effective amount of a pharmaceutical composition. The pharmaceutical composition includes an RRAmod. The therapeutically effective amount of an RRAmod is an amount effective to inhibit neoplastic cell growth in the subject.

In yet another aspect, a pharmaceutical composition is provided. The pharmaceutical composition includes an RRAmod. The RRAmod inhibits cell growth when administered to a neoplastic cell.

DETAILED DESCRIPTION

Figure 1:
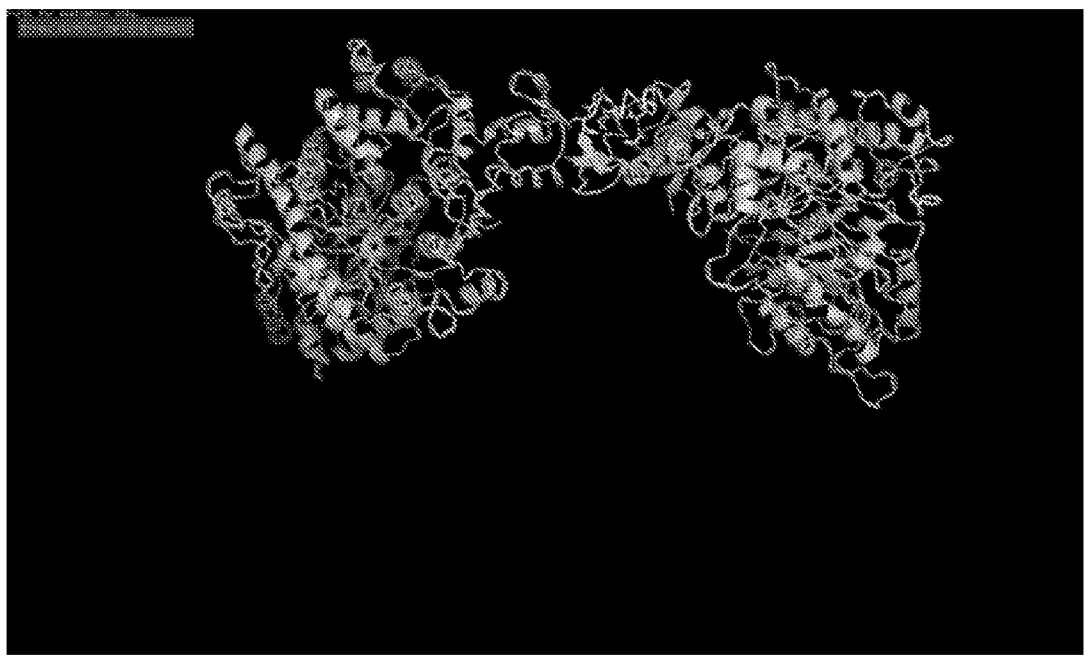
FIG. 1 illustrates a ribbon diagram indentifying the hexamer interface on ribonucleotide reductase that is targeted by small molecules.
Figure 2:
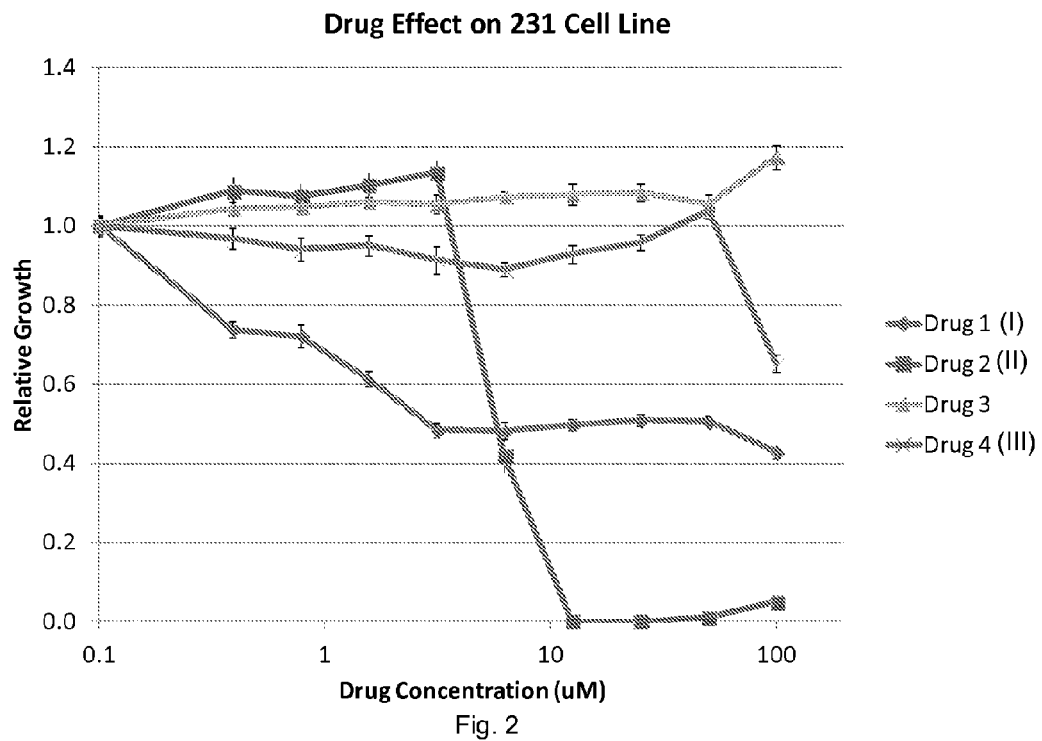
FIG. 2 is a graph showing the drug effects of Drug 1, Drug 2, Drug 3 and Drug 4 on the 231 triple negative breast cell line.
Figure 3:
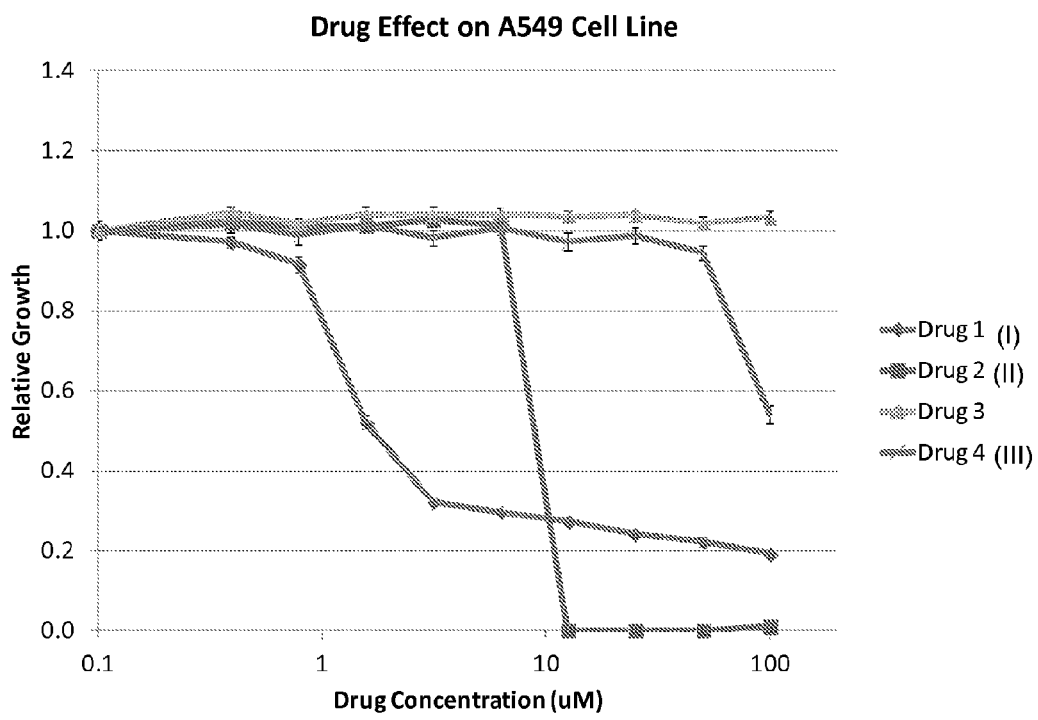
FIG. 3 is a graph showing the drug effects of Drug 1, Drug 2, Drug 3 and Drug 4 on the A549 non-small lung cell line.
Figure 4:
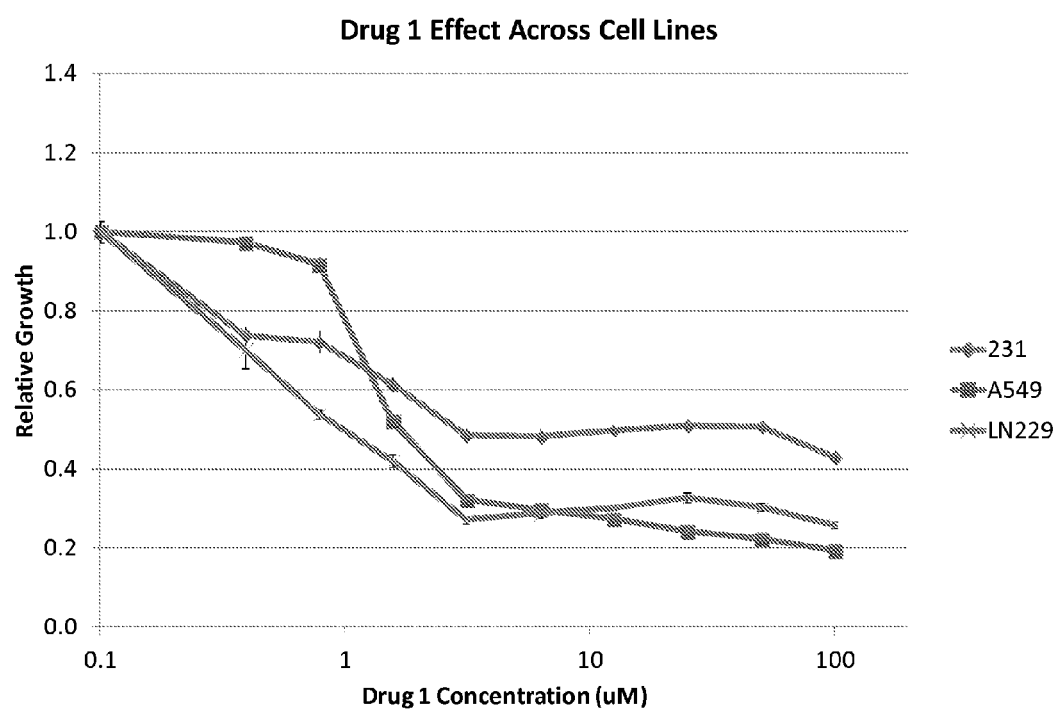
FIG. 4 is a graph showing the drug effect of Drug 1 on the 231 triple negative breast, A549 non-small lung and LN229 glioblastoma cell lines.
Figure 5:
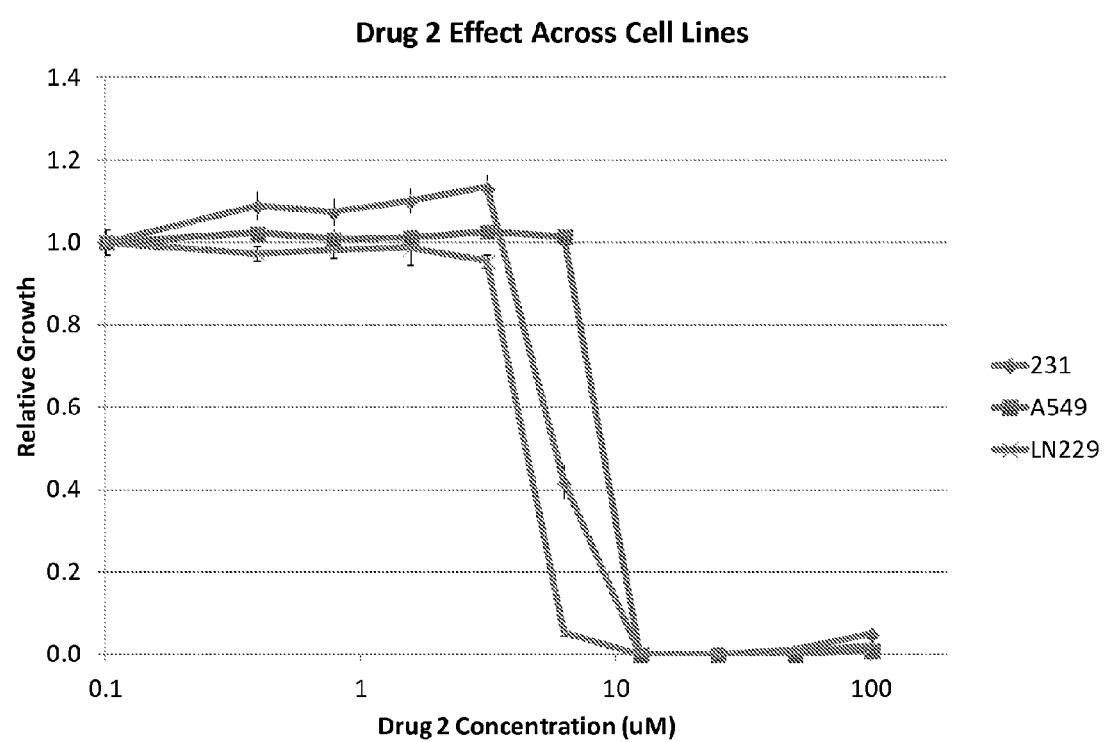
FIG. 5 is a graph showing the drug effect of Drug 2 on the 231 triple negative breast, A549 non-small lung and LN229 glioblastoma cell lines.
Figure 6:
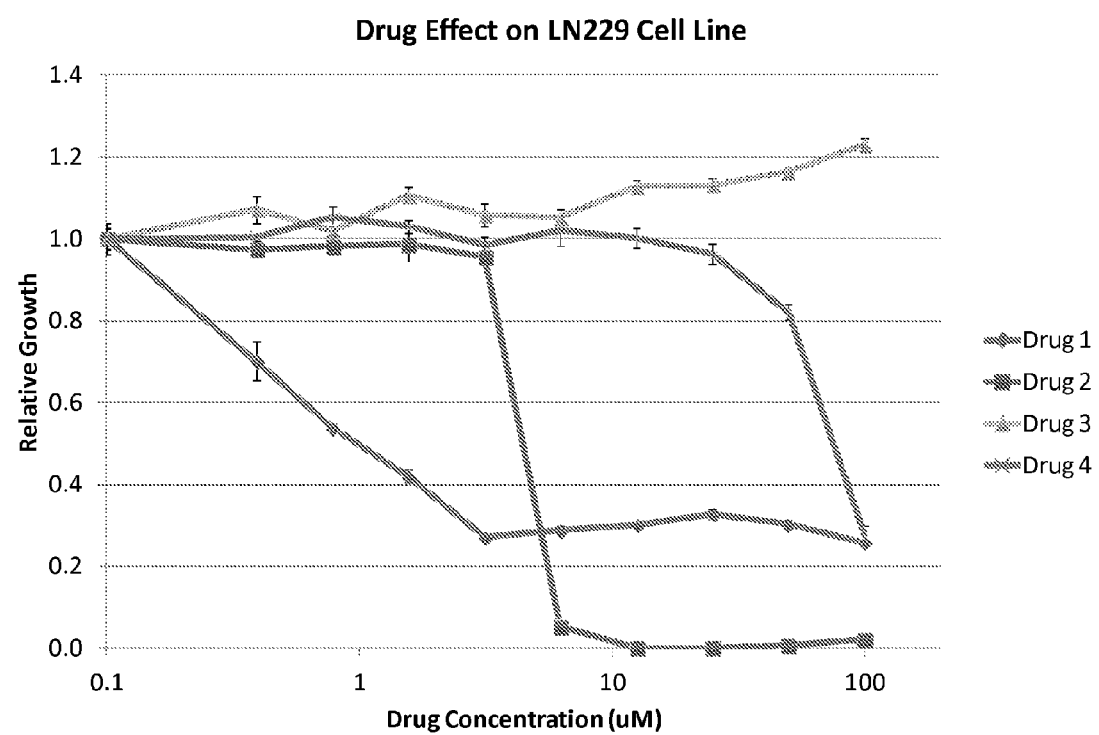
FIG. 6 is a graph showing the drug effects of Drug 1, Drug 2, Drug 3 and Drug 4 on the LN229 glioblastoma cell line.
Figure 7:
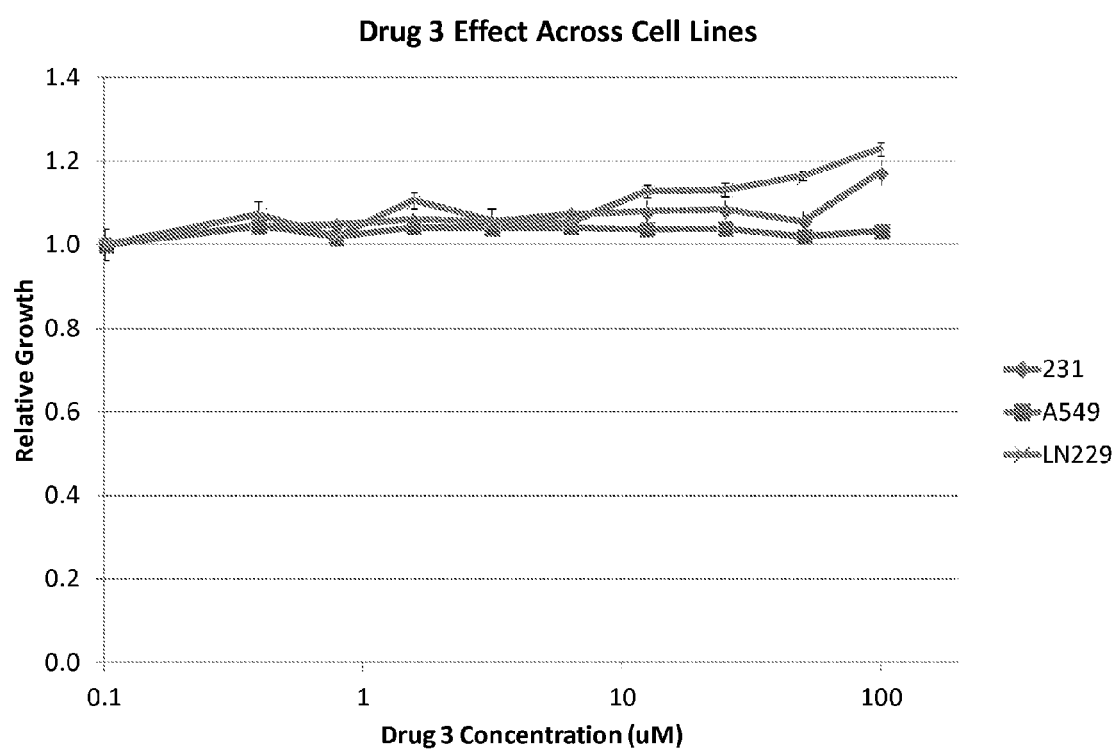
FIG. 7 is a graph showing the drug effect of Drug 3 (compound not shown) on the 231 triple negative breast, A549 non-small lung and LN229 glioblastoma cell lines.
Figure 8:
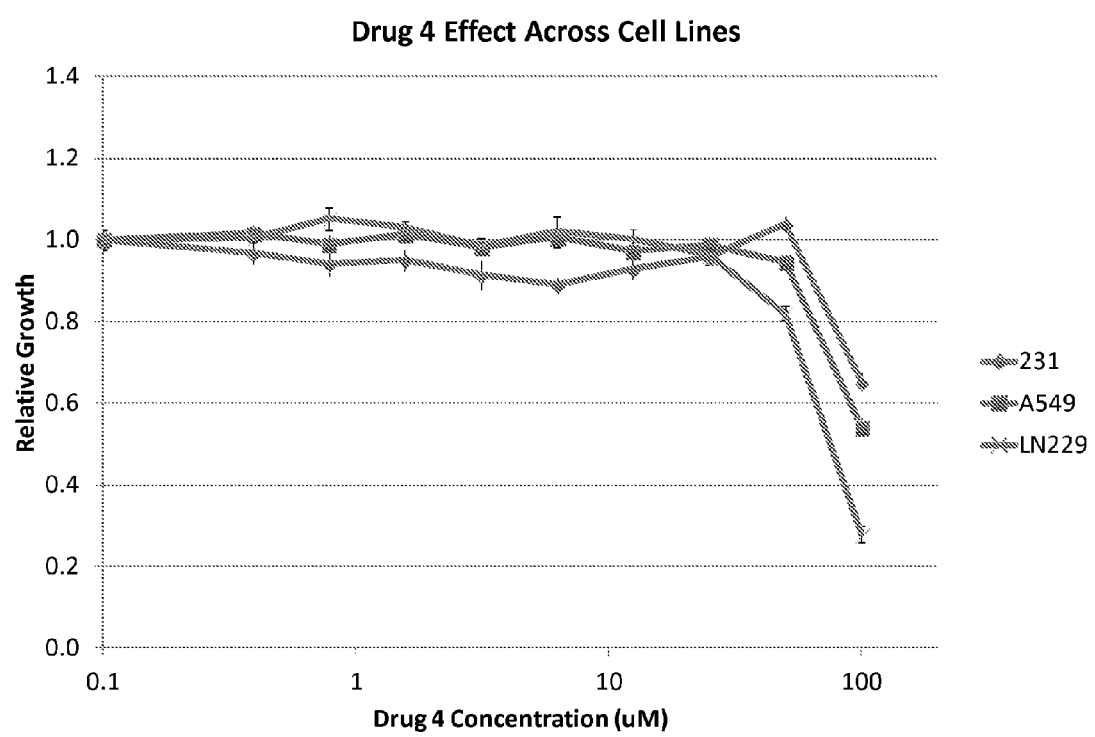
FIG. 8 is a graph showing the drug effect of Drug 4 on the 231 triple negative breast, A549 non-small lung and LN229 glioblastoma cell lines.

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

The term "allosteric" refers to or denotes the alteration of the activity of a protein (e.g., an enzyme) through the binding of an effector molecule at a specific binding site. Effectors that decrease or increase the protein's activity are referred to as "allosteric modulators". An "allosteric site" as used herein relates to or denotes the site on an enzyme molecule which binds with a nonsubstrate molecule, inducing a conformational change that results in an alteration of the affinity of the enzyme for its substrate thereby modulating the enzyme's activity. The phrase "having the formula" or "having the structure" is not intended to be limiting and is used in the same way that the term "comprising" is commonly used.

The term "alkyl" refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups, such as cyclopentyl, cyclohexyl, and the like. Generally, although again not necessarily, alkyl groups herein contain 1 to about 18 carbon atoms, preferably 1 to about 12 carbon atoms. The term "lower alkyl" intends an alkyl group of 1 to 6 carbon atoms. Substituents identified as "$C_1$-$C_6$ alkyl" or "lower alkyl" can contain 1 to 3 carbon atoms, and more particularly such substituents can contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 20 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The term "cyclic" refers to alicyclic or aromatic substituents that may or may not be substituted and/or heteroatom containing, and that may be monocyclic, bicyclic, or polycyclic.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

The term "hydrocarbyl" refers to univalent hydrocarbyl radicals containing 1 to about 30 carbon atoms, preferably 1 to about 24 carbon atoms, more preferably 1 to about 18 carbon atoms, most preferably about 1 to 12 carbon atoms, including linear, branched, cyclic, saturated, and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—ON$^+$C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

When referring to a compound described herein, the term "compound" is meant to encompass not only the specified molecular entity but also its pharmaceutically acceptable, pharmacologically active analogs, including, but not limited to, salts, esters, amides, prodrugs, conjugates, active metabolites, and other such derivatives, analogs, and related compounds.

Some of the compounds disclosed herein may contain one or more asymmetric centers and may thus give rise to enantiomers, diastereomers, and other stereoisomeric forms. The present invention is also meant to encompass racemic mixtures, resolved forms and mixtures thereof, as well as the individual enantiomers that may be separated according to methods that are well know to those of ordinary skill in the art. When the compounds described herein contain olefinic double bonds or other centers of geometric asymmetry, and unless specified otherwise, it is intended to include both E and Z geometric isomers.

The term "stereoisomers" is a general term for all isomers of individual molecules that differ only in the orientation of their atoms in space. It includes enantiomers and isomers of compounds with more than one chiral center that are not minor images of one another (diastereomers).

The term "asymmetric center" or "chiral center" refers to a carbon atom to which four different groups are attached.

The term "enantiomer" or "enantiomeric" refers to a molecule that is nonsuperimposeable on its minor image and hence optically active wherein the enantiomer rotates the plane of polarized light in one direction and its minor image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule. The phrase "enantiomeric excess" refers to a mixture wherein one enantiomer is present is a greater concentration than its mirror image molecule.

The term "epitope" refers to a physical structure on a molecule that interacts with a selective component. In exemplary embodiments, epitope refers to a desired region on a target molecule that specifically interacts with a selectivity component.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" derivative or analog, refers to a derivative or analog having the same type of pharmacological activity as the parent compound and approximately equivalent in degree.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, phosphoric acid and the like. Pharmaceutical salts can also be obtained by reacting a compound with an organic acid such as aliphatic or aromatic carboxylic or sulfonic acids, for example acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, C1-C7 alkylamine, cyclohexylamine, triethanolamine, ethylenediamine, and salts with amino acids such as arginine, lysine, and the like.

The term "small molecule" refers to a low molecular weight organic compound, which is by definition not a polymer. The small molecule can bind with high affinity to a biopolymer, such as protein, nucleic acid, or polysaccharide and in some instances alter the activity or function of the biopolymer. The upper molecular weight limit for a small molecule is about 800 Daltons, which allows for the possibility to rapidly diffuse across cell membranes so that they can reach intracellular sites of action. In addition, this molecular weight cutoff is a necessary but insufficient condition for oral bioavailability.

The term "anticancer agent" refers to a compound which treats a cancer (e.g., a compound which is useful in the treatment of a cancer). The anticancer effect(s) may arise through one or more mechanisms including, but not limited to, the regulation of cell proliferation, the inhibition of cell cycle progression, the inhibition of cell growth, the inhibition of angiogenesis, the inhibition of metastasis, the inhibition of invasion (e.g., the spread of tumor cells into healthy neighboring tissue), or the promotion of apoptosis. The term "antineoplastic" is used herein to mean a chemotherapeutic intended to inhibit or prevent the maturation and proliferation of neoplasms, by targeting the DNA.

The term "cell growth" is used in the contexts of cell development and cell division (reproduction). When used in the context of cell division, it refers to growth of cell populations, where one cell (the "mother cell") grows and divides to produce two "daughter cells" (M phase). When used in the context of cell development, the term refers to increase in cytoplasmic and organelle volume (G1 phase), as well as increase in genetic material before replication (G2 phase).

The terms "neoplastic cell", "cancer cell" or "tumor cell" refer to cells that divide at an abnormal (i.e., increased) rate. A neoplastic cell or neoplasm (tumor) can be benign, potentially malignant, or malignant. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, meningoma, medulloblastoma, schwannoma and epidymoma.

The term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder (e.g., a neoplastic disorder). The term "patient" includes human and veterinary subjects. In some aspects of the disclosed methods, the subject has been diagnosed with a need for treatment of one or more neoplastic disorders prior to the administering step. In some aspects of the disclosed method, the subject has been diagnosed with a need for allosteric inhibition of ribonucleotide reductase enzyme activity prior to the administering step.

The terms "treating" or "treatment" of a condition may refer to preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition' or some combination thereof. With regard to neoplastic disorders, "treating" or "treatment" may refer to inhibiting or slowing neoplastic and/or malignant cell growth, proliferation, and/or metastasis, preventing or delaying the development of neoplastic and/or malignant cell growth, proliferation, and/or metastasis, or some combination thereof. With regard to a tumor, "treating" or "treatment" may refer to eradicating all or part of a tumor, inhibiting or slowing tumor growth and metastasis, preventing or delaying the development of a tumor, or some combination thereof.

The phrase "therapeutically effective amount" refers to an amount of a compound that produces a desired therapeutic effect. In one aspect, the therapeutically effective amount is the amount required to inhibit neoplastic cell growth in the subject. The precise therapeutically effective amount is an amount of the composition that will yield the most effective results in terms of efficacy in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy (Gennaro ed. 22nd Edition, Pharmaceutical Press, London, UK, 2012).

The terms "$IC_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition of de novo DNA synthesis, cell growth or a surrogate thereof.

The terms "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. In exemplary embodiments, antibodies used with the methods and compositions described herein are derivatives of the IgG class.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')$_2$, scFv, Fv, dsFv diabody, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

As used herein, the term "diabodies" refers to dimeric scFvs. The components of diabodies typically have shorter peptide linkers than most scFvs and they show a preference for associating as dimers.

The term "epitope" refers to a physical structure on a molecule that interacts with a selective component. In exemplary embodiments, epitope refers to a desired region on a target molecule that specifically interacts with a selectivity component.

The term "Fab" refers to an antibody fragment that is essentially equivalent to that obtained by digestion of immunoglobulin (typically IgG) with the enzyme papain. The heavy chain segment of the Fab fragment is the Fd piece. Such fragments may be enzymatically or chemically produced by fragmentation of an intact antibody, recombinantly produced from a gene encoding the partial antibody sequence, or it may be wholly or partially synthetically produced.

The term "Fab'" refers to an antibody fragment that is essentially equivalent to that obtained by reduction of the disulfide bridge or bridges joining the two heavy chain pieces in the F(ab')$_2$ fragment. Such fragments may be enzymatically or chemically produced by fragmentation of an intact antibody, recombinantly produced from a gene encoding the partial antibody sequence, or it may be wholly or partially synthetically produced.

The term "F(ab')$_2$" refers to an antibody fragment that is essentially equivalent to a fragment obtained by digestion of an immunoglobulin (typically IgG) with the enzyme pepsin at pH 4.0-4.5. Such fragments may be enzymatically or chemically produced by fragmentation of an intact antibody, recombinantly produced from a gene encoding the partial antibody sequence, or it may be wholly or partially synthetically produced.

The term "Fv" refers to an antibody fragment that consists of one $V_H$ and one $V_L$ domain held together by noncovalent interactions. The term "dsFv" is used herein to refer to an Fv with an engineered intermolecular disulfide bond to stabilize the $V_H$-$V_L$ pair.

The terms "single-chain Fvs" and "scFvs" refers to recombinant antibody fragments consisting of only the variable light chain ($V_L$) and variable heavy chain ($V_H$) covalently connected to one another by a polypeptide linker. Either $V_L$ or $V_H$ may be the $NH_2$-terminal domain. The polypeptide linker may be of variable length and composition so long as the two variable domains are bridged without serious steric interference. In exemplary embodiments, the linkers are comprised primarily of stretches of glycine and serine residues with some glutamic acid or lysine residues interspersed for solubility.

Embodiments described herein relate to ribonucleotide reductase allosteric modulators (RRAmods), pharmaceutical compositions comprising RRAmods, therapeutic uses of RRAmods, as well as compounds found to be specifically effective as allosteric modulators of ribonucleotide reductase activity in neoplastic cells.

Using X-ray crystallography, we mapped a hexamer interface epitope of the large subunit of ribonuecleotide reductase (RR) (see FIG. 1) and found that it could be targeted by small molecules to modulate ribonucleotide reductase activity. The epitope found to be in the hexamer interface is part of an allosteric site of RR1, known as the activity site (A-site). The epitope has the amino acid sequence MHVIKRDGRQERVMFDKITSR (SEQ ID NO:1), which corresponds to residues 1 to 21 of the 30 amino acid long N terminus of the RR1 subunit. Small molecules that bind to or complex with this region of ribonucleotide reductase were found to allosterically modulate (e.g., inhibit or activate) the enzyme.

Ribonucleotide reductase enzyme activity is required for de novo DNA synthesis by catalyzing ribonucleotides to deoxy ribonucleotides and maintaining a balanced nucleotide precursor molecule pool. Since the proliferation of cancer cells requires excess dNTPs for DNA synthesis, RRAmods that specifically target the hexamer interface of RR1 can be employed to inhibit cell growth and proliferation of neoplastic cells through the modulation of ribonucleotide reductase enzyme activity. Therefore, in some embodiments described herein, a method of modulating ribonucleotide reductase activity in a neoplastic cell can include administering to the neoplastic cell an amount of an RRAmod effective to inhibit neoplastic cell growth.

RRAmods described herein include agents capable of binding to or complexing with the hexamer interface of ribonucleotide reductase and allosterically modulating ribonucleotide reductase enzyme activity, thereby affecting de novo DNA synthesis, cell growth and proliferation of neoplastic cells. RRAmods can include organic compounds, peptides, inorganic compounds, lipids, peptidomimetics, antibodies or fragments thereof and small molecule synthetic compounds.

In some embodiments, the RRAmod is an antibody that selectively or specifically binds to the hexamer interface of ribonucleotide reductase. In certain embodiments, the antibody can specifically bind to SEQ ID NO: 1. The antibody can be a monoclonal antibody, a polyclonal antibody, or a humanized antibody including without limitation: Fv fragments, single chain Fv (scFv) fragments, Fab' fragments, F(ab')2 fragments, single domain antibodies, camelized antibodies and antibody fragments, humanized antibodies and antibody fragments, and multivalent versions of the foregoing; multivalent targeting moieties including without limitation: monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; and receptor molecules, which naturally interact with a desired target molecule.

Preparation of antibodies may be accomplished by any number of well-known methods for generating monoclonal antibodies. These methods typically include the step of immunization of animals, typically mice, with a desired immunogen (e.g., a desired target molecule or fragment thereof). Once the mice have been immunized, and preferably boosted one or more times with the desired immunogen (s), monoclonal antibody-producing hybridomas may be prepared and screened according to well known methods. See, for example, Kuby, Janis, Immunology, Third Edition, pp. 131-139, W.H. Freeman & Co. (1997), for a general overview of monoclonal antibody production, that portion of which is incorporated herein by reference.

In certain embodiments, the RRAmod is a small molecule. Exemplary data of small molecule compounds found to be specifically effective as allosteric modulators of ribonucleotide reductase activity are provided in the Example below. In particular, the disclosed compounds had activity in modulating the ribonucleotide reductase activity in DNA synthesis assays, generally with an IC$_{50}$ for inhibition or activation of less than about 70 μM. Certain compounds described herein have an IC$_{50}$ for killing carcinomas in a cell-based assay of less than about 2 μM.

In one embodiment, an RRAmod can include a small molecule having the formula (I):

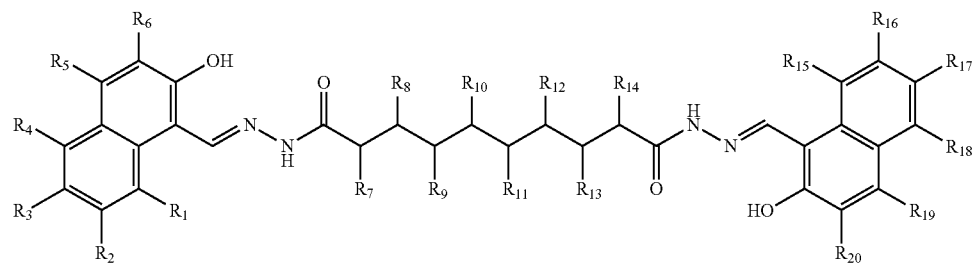

wherein each of $R_1$ to $R_{20}$ can be independently selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), combinations thereof, and wherein adjacent R groups may be linked to form a cyclic or polycyclic ring, wherein the cyclic ring is aromatic, alicyclic, heteroaromatic, or heterocyclic; or a pharmaceutically acceptable salt thereof.

In other embodiments, each of $R_1$ to $R_{20}$ can be independently selected from hydrogen, alkyl, branched alkyl, cycloalkyl, halogen, a heteratom, or a pharmaceutically acceptable salt thereof.

In certain embodiments, an RRAmod having formula (I) can be:

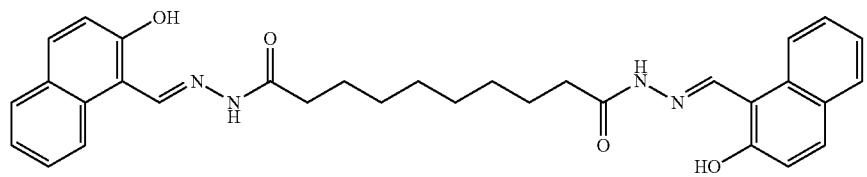 [SMILES: O=C(CCCCCCCCC(=O)N/N=C/c1c(O)ccc2ccccc12)N/N=C/c1c(O)ccc2ccccc12]

or a pharmaceutically acceptable salt thereof.

In another embodiment, the RRAmod can be a small molecule having the formula (II):

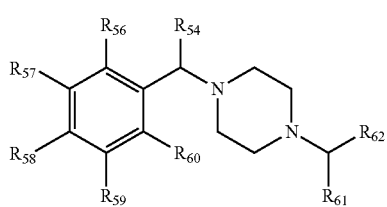

wherein each of $R_{54}$ to $R_{62}$ can be independently selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), combinations thereof, and wherein adjacent R groups may be linked to form a cyclic or polycyclic ring, wherein the cyclic ring is aromatic, alicyclic, heteroaromatic, or heterocyclic; or a pharmaceutically acceptable salt thereof.

In certain embodiments, an RRAmod having formula (II) can have the following formula (III):

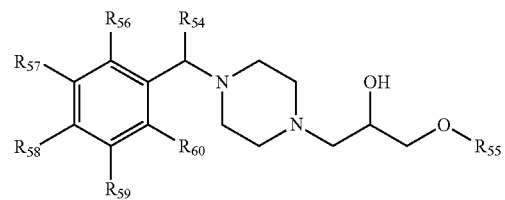

wherein each of $R_{54}$ to $R_{60}$ can be independently selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—

O-aryl), carboxy (—COOH), carboxylato (—COO⁻), carbamoyl (—(CO)—NH$_2$), C$_1$-C$_{24}$ alkyl-carbamoyl (—(CO)—NH(C$_1$-C$_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N⁺C⁻), cyanato (—O—CN), isocyanato (—O—N⁺=C⁻), isothiocyanato (—S—CN), azido (—N=N⁺=N⁻), formyl (—(CO)—H), thioformyl (—(CS)—H), amino (—NH$_2$), C$_1$-C$_{24}$ alkyl amino, C$_5$-C$_{20}$ aryl amino, C$_2$-C$_{24}$ alkylamido (—NH—(CO)-alkyl), C$_6$-C$_{20}$ arylamido (—NH—(CO)-aryl), imino (—CR=NH where R is hydrogen, C$_1$-C$_{24}$ alkyl, C$_5$-C$_{20}$ aryl, C$_6$-C$_{24}$ alkaryl, C$_6$-C$_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O⁻), C$_1$-C$_{24}$ alkylsulfanyl (—S-alkyl; also termed "alkylthio"), arylsulfanyl (—S-aryl; also termed "arylthio"), C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), phosphono (—P(O)(OH)$_2$), phosphonato (—P(O)(O⁻)$_2$), phosphinato (—P(O)(O⁻)), phospho (—PO$_2$), phosphino (—PH$_2$), combinations thereof, and wherein adjacent R groups may be linked to form a cyclic or polycyclic ring, wherein the cyclic ring is aromatic, alicyclic, heteroaromatic, or heterocyclic; or a pharmaceutically acceptable salt thereof.

In some embodiments, an RRmodA having formula (III) can be selected from the group consisting of:

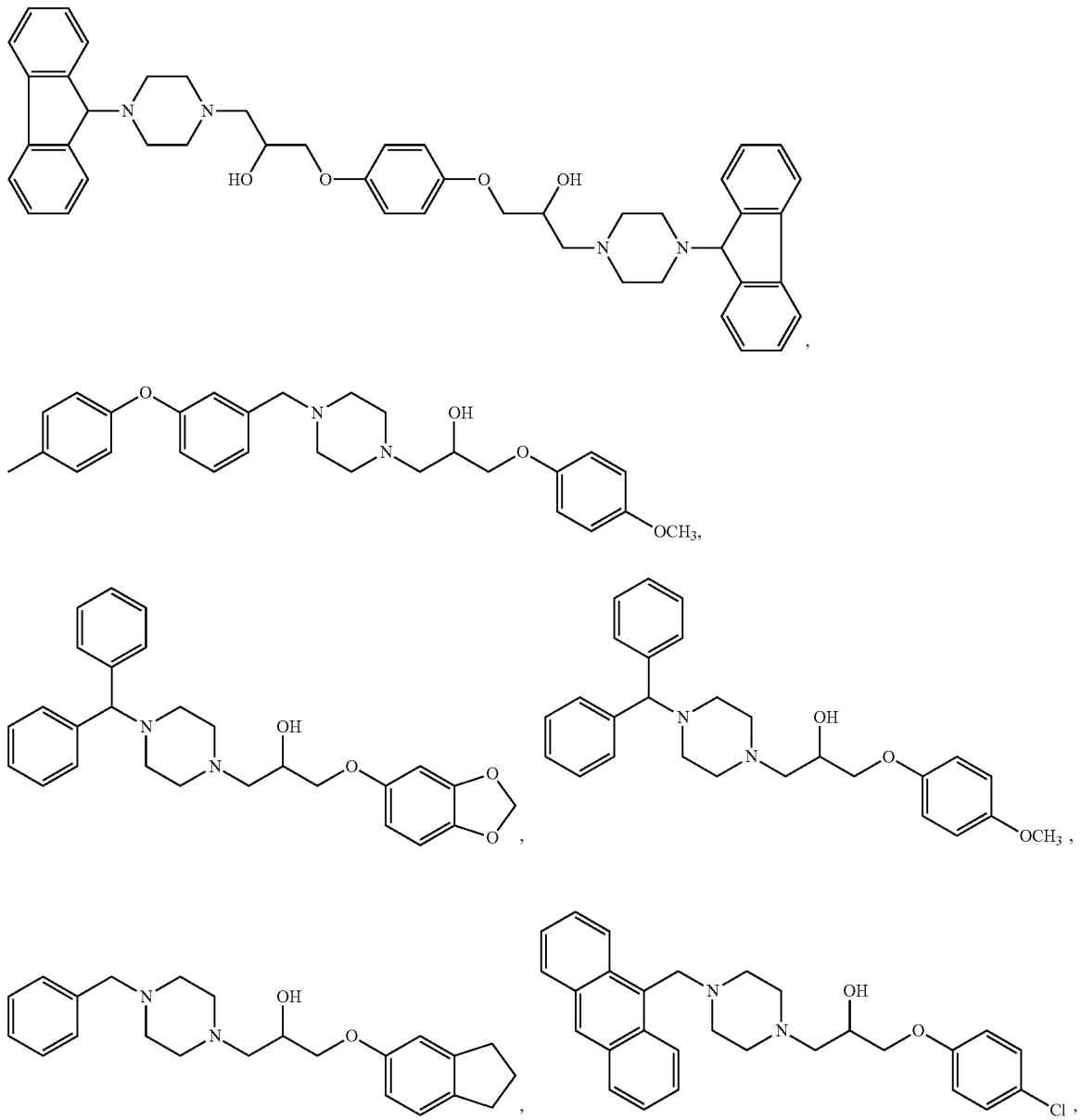

and pharmaceutically acceptable salts thereof.

In still other embodiments, an RRAmod having formula (II) can have the following formula:

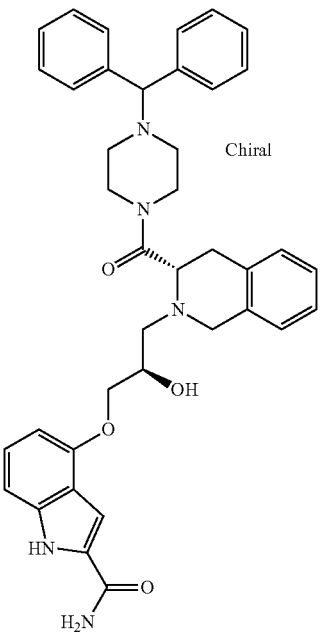 [SMILES: NC(=O)c1cc2c(OC[C@H](O)CN3Cc4ccccc4C[C@H]3C(=O)N3CCN(C(c4ccccc4)c4ccccc4)CC3)cccc2[nH]1]

or be a pharmaceutically acceptable salt thereof.

In another embodiment, the RRAmod can be a small molecule having the formula (IV):

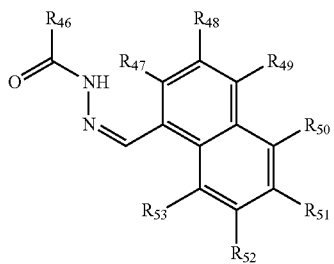

wherein each of $R_{46}$ to $R_{53}$ can be independently selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N⁺C⁻), cyanato (—O—CN), isocyanato (—O—N⁺=C⁻), isothiocyanato (—S—CN), azido (—N=N⁺=N⁻), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O⁻), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O⁻)$_2$), phosphinato (—P(O)(O⁻)), phospho (—PO$_2$), phosphino (—PH$_2$), combinations thereof, and wherein adjacent R groups may be linked to form a cyclic or polycyclic ring, wherein the cyclic ring is aromatic, alicyclic, heteroaromatic, or heterocyclic; or a pharmaceutically acceptable salt thereof.

In certain embodiments, an RRAmod having formula (IV) can have the following formula (V):

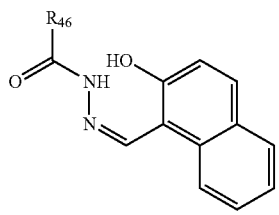

wherein $R_{46}$ can be selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N⁺C⁻), cyanato (—O—CN), isocyanato (—O—N⁺=C⁻), isothiocyanato (—S—CN), azido (—N=N⁺=N⁻), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O⁻), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O⁻)₂), phosphinato (—P(O)(O⁻)), phospho (—PO₂), phosphino (—PH₂), combinations thereof, or a pharmaceutically acceptable salt thereof.

In some embodiments, an RRmodA having formula (V) can be selected from the group consisting of:

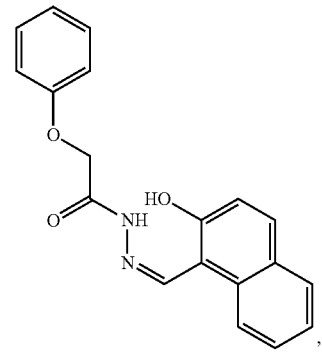

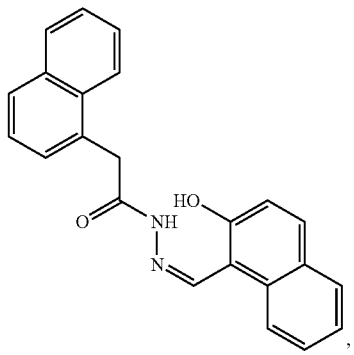

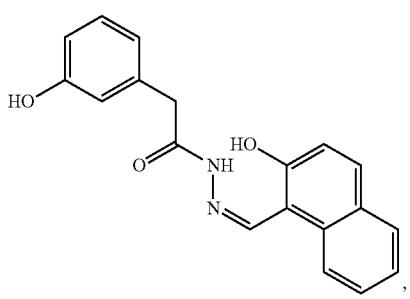

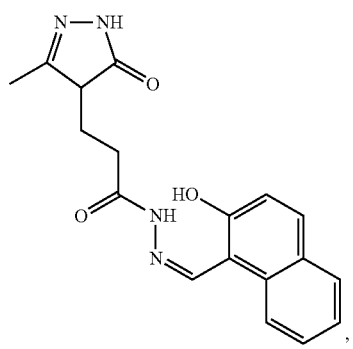

-continued

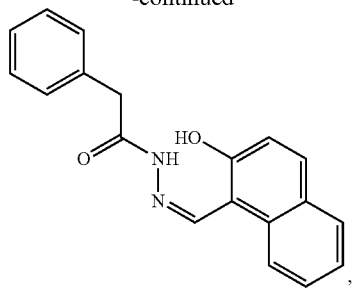

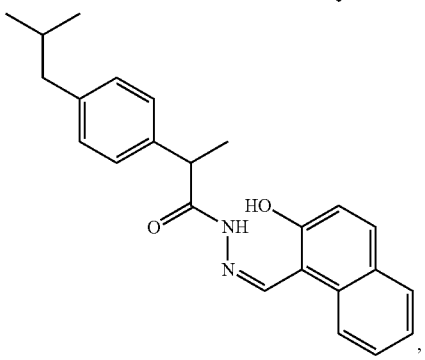

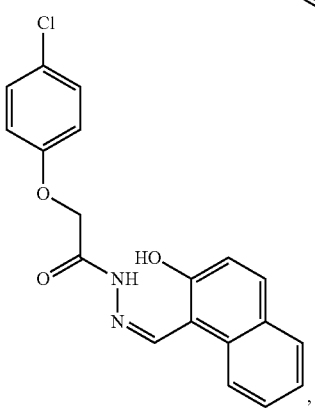

and pharmaceutically acceptable salts thereof.

In certain embodiments, an RRAmod having formula (IV) can have the following formula (VI):

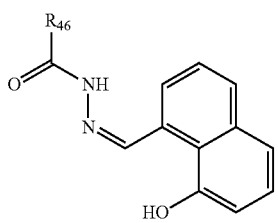

wherein $R_{46}$ can be selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH₂), C₁-C₂₄ alkyl-carbamoyl (—(CO)—NH(C₁-C₂₄ alkyl)), arylcarbamoyl (—(CO)—NH-aryl), thiocarbamoyl (—(CS)—NH₂), carbamido (—NH—(CO)—NH₂), cyano(—CN), isocyano (—N⁺C⁻), cyanato (—O—CN), isocyanato (—O—N⁺=C⁻), isothiocyanato (—S—CN), azido (—N=N⁺=N⁻), formyl (—(CO)—H), thioformyl (—(CS)—H), amino (—NH₂), C₁-C₂₄ alkyl amino, C₅-C₂₀ aryl amino, C₂-C₂₄ alkylamido (—NH—(CO)-alkyl), C₆-C₂₀ arylamido (—NH—(CO)-aryl), imino (—CR=NH where R is hydrogen, C₁-C₂₄ alkyl, C₅-C₂₀ aryl, C₆-C₂₄ alkaryl, C₆-C₂₄ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO₂), nitroso (—NO), sulfo (—SO₂—OH), sulfonato (—SO₂—O⁻), C₁-C₂₄ alkylsulfanyl (—S-alkyl; also termed "alkylthio"), arylsulfanyl (—S-aryl; also termed "arylthio"), C₁-C₂₄ alkylsulfinyl (—(SO)-alkyl), C₅-C₂₀ arylsulfinyl (—(SO)-aryl), C₁-C₂₄ alkylsulfonyl (—SO₂-alkyl), C₅-C₂₀ arylsulfonyl (—SO₂-aryl), phosphono (—P(O)(OH)₂), phosphonato (—P(O)(O⁻)₂), phosphinato (—P(O)(O⁻)), phospho (—PO₂), phosphino (—PH₂), combinations thereof, or a pharmaceutically acceptable salt thereof.

In some embodiments, an RRmodA having formula (VI) can be:

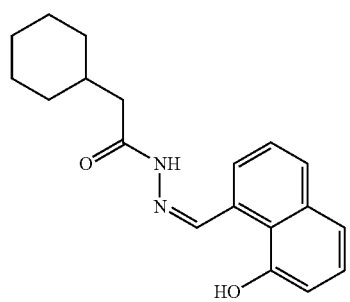 [SMILES: O=C(CC1CCCCC1)N/N=C\c1cccc2cccc(O)c12]

or a pharmaceutically acceptable salt thereof.

In another embodiment, an RRAmod can include a small molecule having the formula (VII):

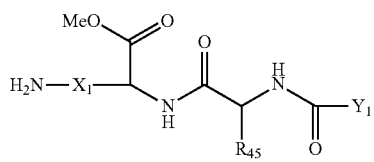

wherein X₁ is a C₁-C₂₄ alkyl, C₂-C₂₄ alkenyl, C₂-C₂₄ alkynyl, Y₁ is a C₁-C₂₄ alkyl, C₂-C₂₄ alkenyl, C₂-C₂₄ alkynyl, and R₄₅ is hydrogen, a C₁-C₂₄ alkyl, C₂-C₂₄ alkenyl, C₂-C₂₄ alkynyl, an amino (—NH₂), or —(C₁-C₂₄ alkyl)-amino, or a pharmaceutically acceptable salt thereof.

In certain embodiments, an RRAmod having formula (VII) can be selected from the group consisting of:

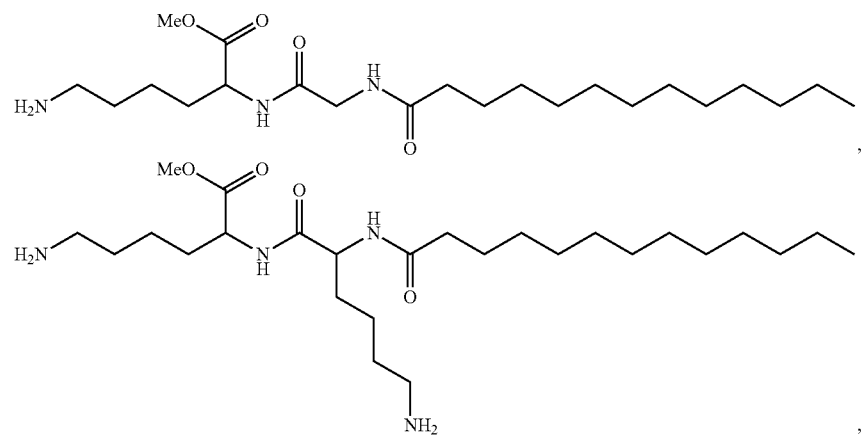

and a pharmaceutically acceptable salt thereof.

In another embodiment, an RRAmod can include a small molecule having the formula (VIII):

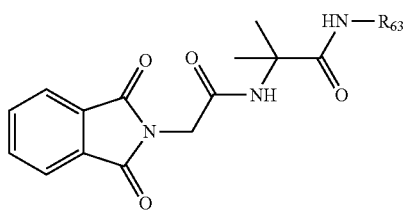

wherein R₆₃ can be selected from the group consisting of hydrogen, C₁-C₂₄ alkyl, C₂-C₂₄ alkenyl, C₂-C₂₄ alkynyl, C₃-C₂₀ aryl, C₆-C₂₄ alkaryl, C₆-C₂₄ aralkyl, halo, silyl, hydroxyl, sulfhydryl, C₁-C₂₄ alkoxy, C₂-C₂₄ alkenyloxy, C₂-C₂₄ alkynyloxy, C₅-C₂₀ aryloxy, acyl (including C₂-C₂₄ alkylcarbonyl (—CO-alkyl) and C₆-C₂₀ arylcarbonyl (—CO-aryl)), acyloxy (—O-acyl), C₂-C₂₄ alkoxycarbonyl (—(CO)—O-alkyl), C₆-C₂₀ aryloxycarbonyl (—(CO)—O-aryl), C₂-C₂₄ alkylcarbonato (—O—(CO)—O-alkyl), C₆-C₂₀ arylcarbonato (—O—(CO)—O-aryl), carboxy (—COOH), carboxylato (—COO⁻), carbamoyl (—(CO)—NH₂), C₁-C₂₄ alkyl-carbamoyl (—(CO)—NH(C₁-C₂₄ alkyl)), arylcarbamoyl (—(CO)—NH-aryl), thiocarbamoyl (—(CS)—NH₂), carbamido (—NH—(CO)—NH₂), cyano(—CN), isocyano (—N⁺C⁻), cyanato (—O—

CN), isocyanato (—O—N⁺=C⁻), isothiocyanato (—S—CN), azido (—N=N⁺=N⁻), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O⁻), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O⁻)$_2$), phosphinato (—P(O)(O⁻)), phospho (—PO$_2$), phosphino (—PH$_2$), combinations thereof, or a pharmaceutically acceptable salt thereof.

In certain embodiments, an RRAmod having formula (VIII) can be:

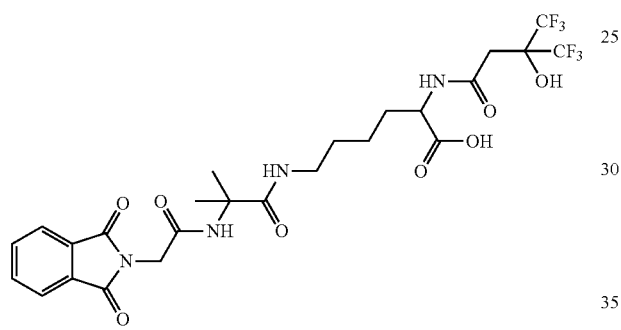

or a pharmaceutically acceptable salt thereof.

In another embodiment, an RRAmod can include a small molecule having the formula (IX):

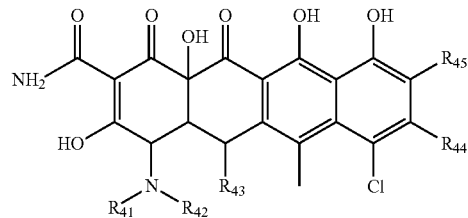

wherein each $R_{41}$ to $R_{45}$ can be independently selected from hydrogen, alkyl, branched alkyl, cyclo-alkyl, halogen, a heteroatom, or a pharmaceutically acceptable salt thereof.

In certain embodiments, an RRAmod having formula (VIII) can be:

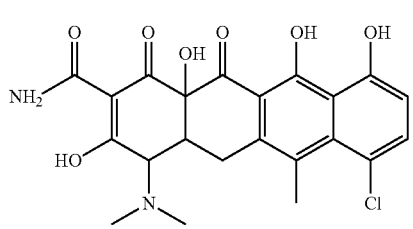 [SMILES: Cc1c2c(c(O)c3c(O)ccc(Cl)c13)C(=O)C1(O)C(=O)C(C(N)=O)=C(O)C(N(C)C)C1C2]

or a pharmaceutically acceptable salt thereof.

In still other embodiments, the RRAmod can be a small molecule selected from the group consisting of:

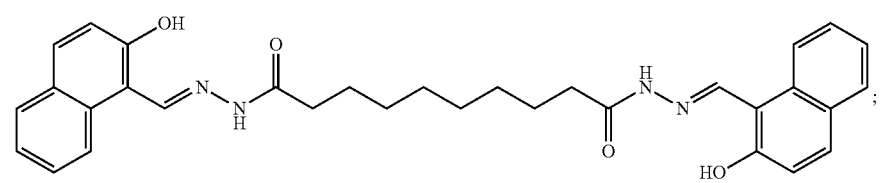

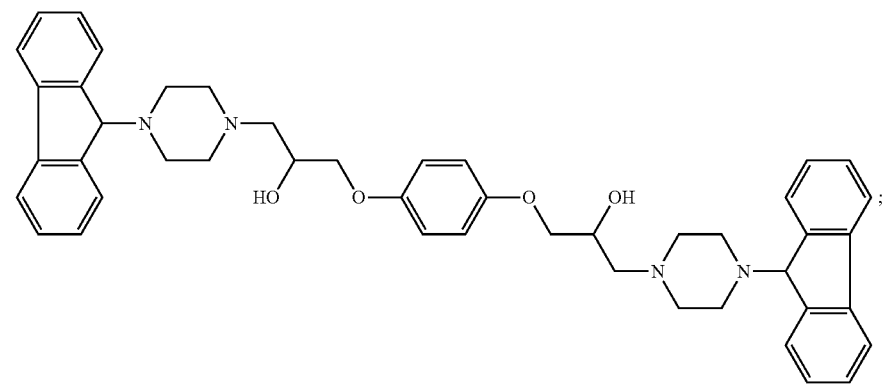

-continued
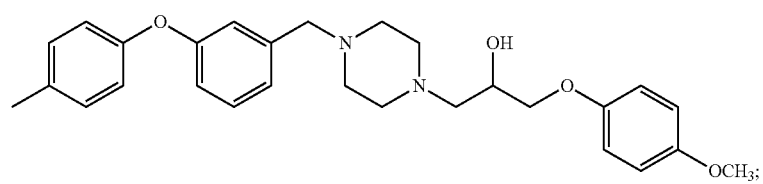
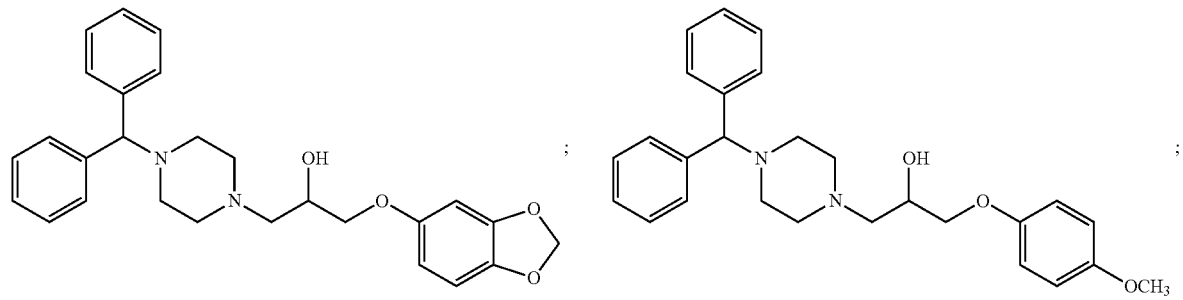
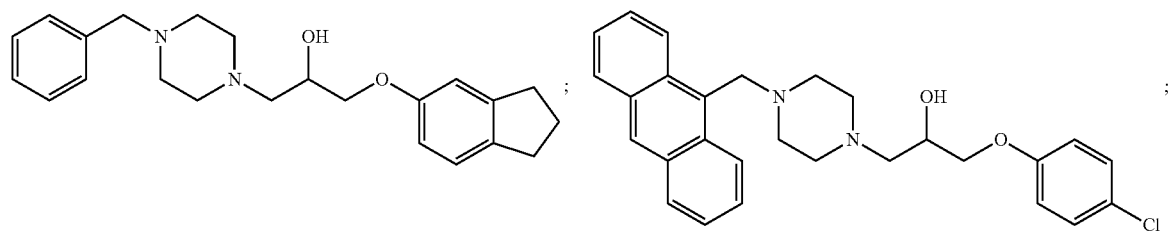
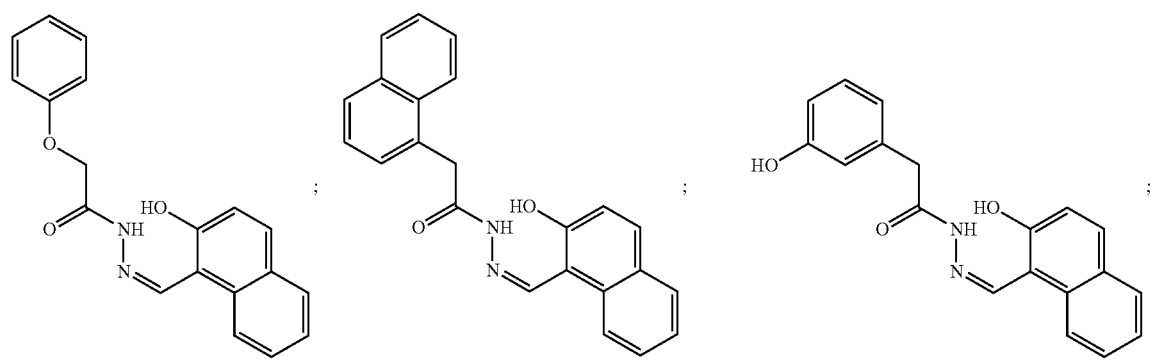
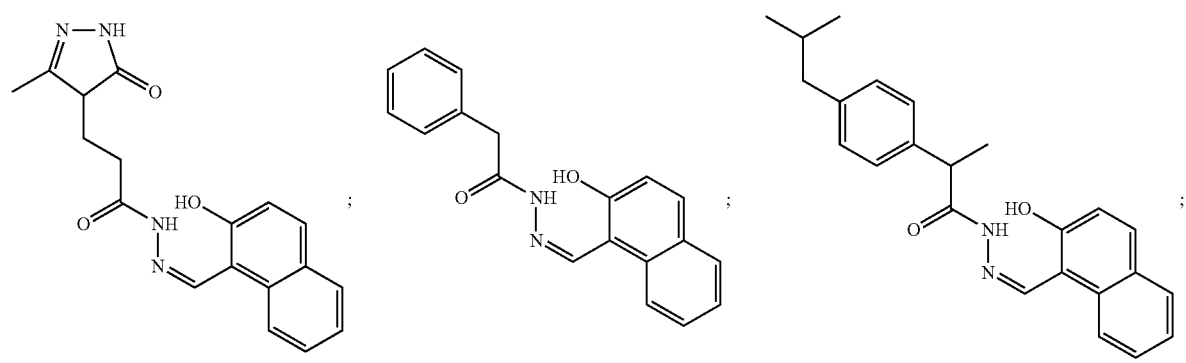

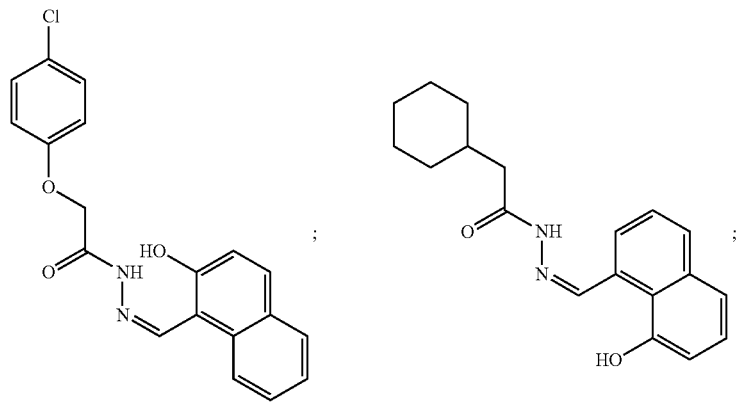

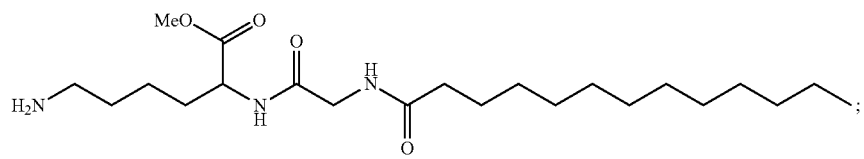

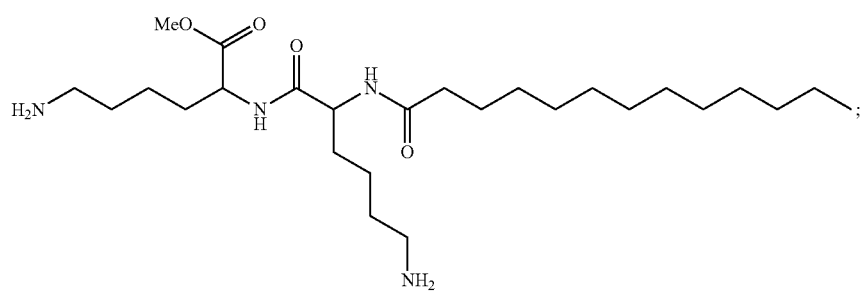

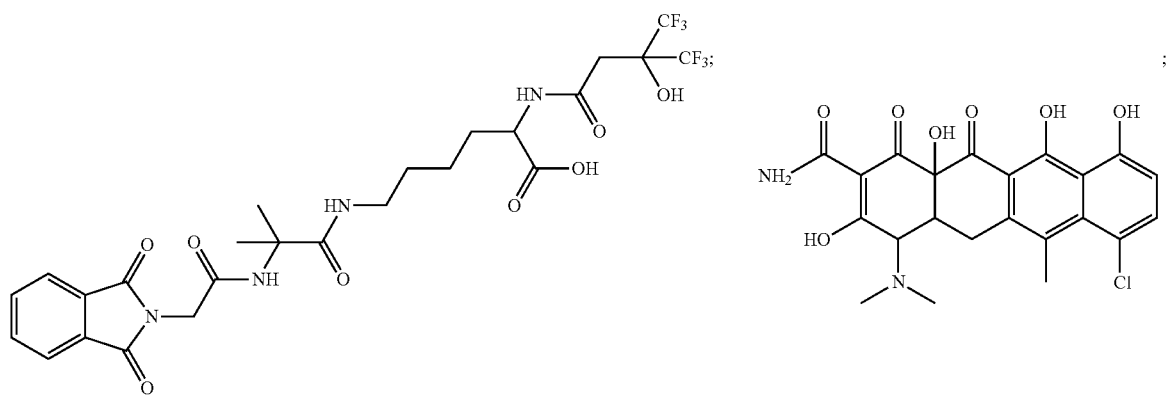

and pharmaceutically acceptable salts thereof.

Additional RRAmods can be identified by screening compounds for the ability to modulate (e.g., inhibit or activate) ribonucleotide reductase enzyme activity. Candidate RRAmods can be screened for function by a variety of techniques known in the art and/or disclosed within the instant application. Candidate compounds may be screened individually, in combination, or as a library of compounds.

Examples of additional RRAmods identified as having the ability to inhibit or activate ribonucleotide reductase enzyme activity include:

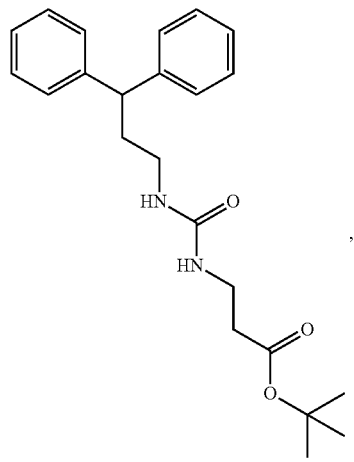,
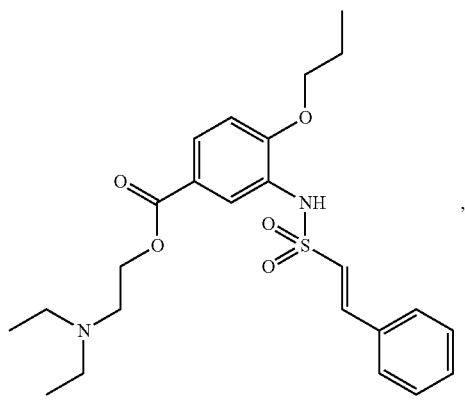,
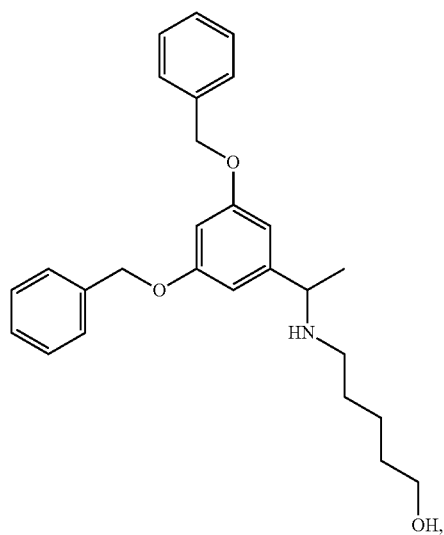,
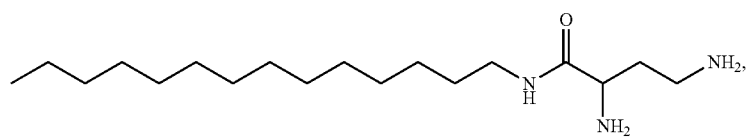
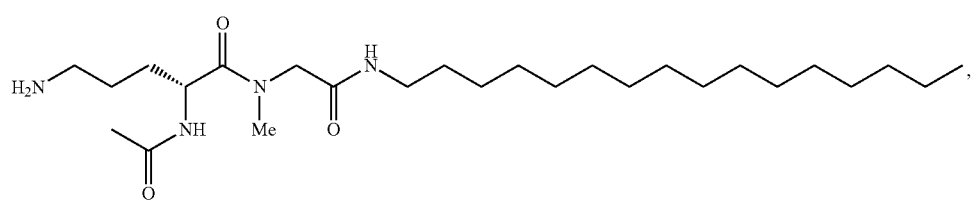,

-continued
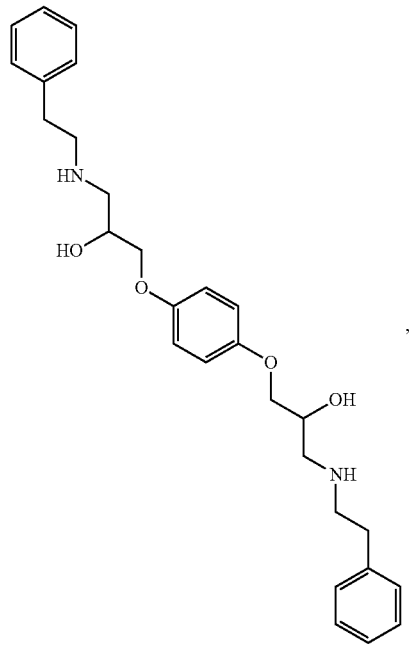
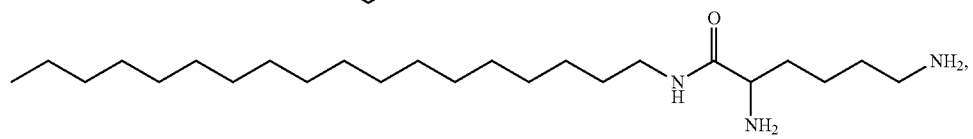
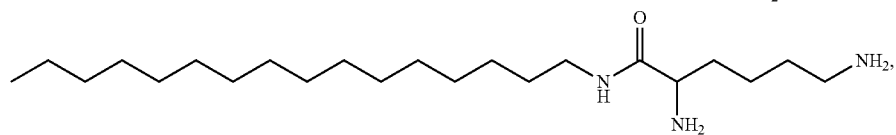
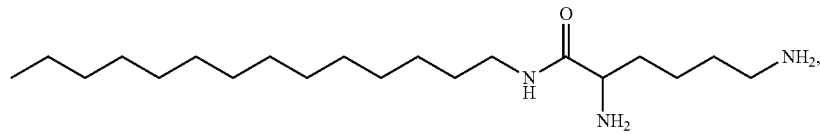
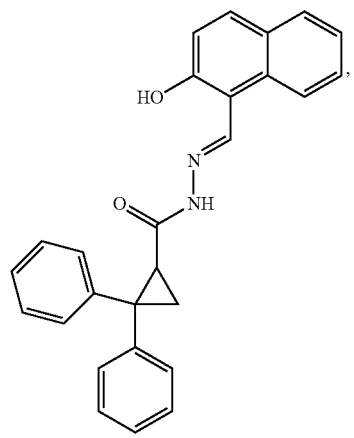
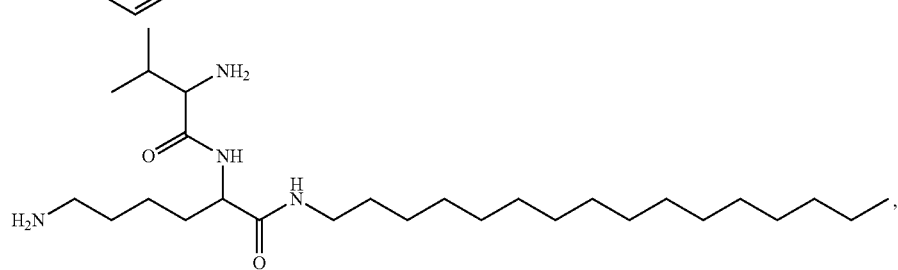

-continued
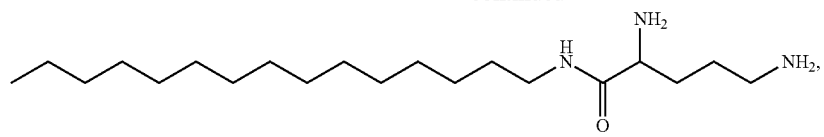
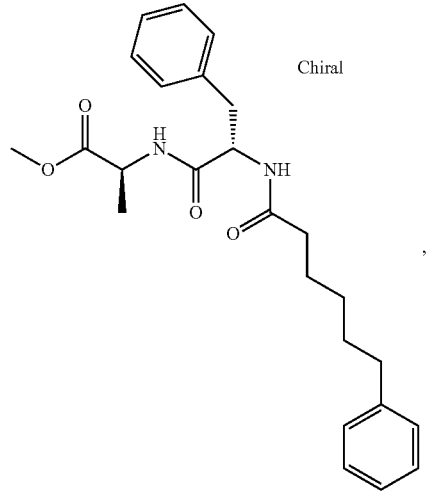
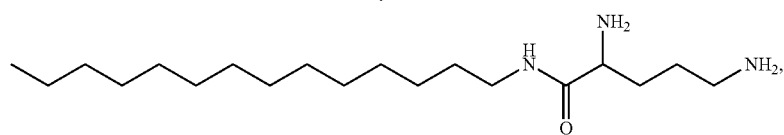
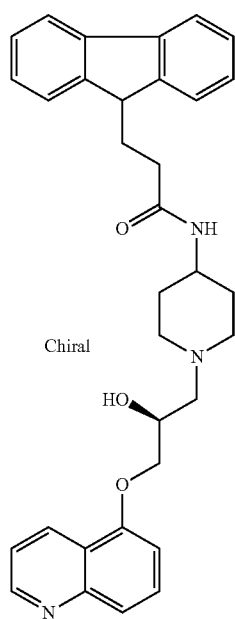
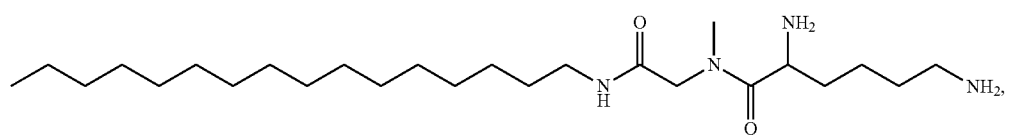
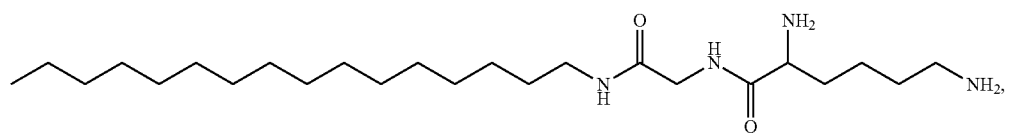

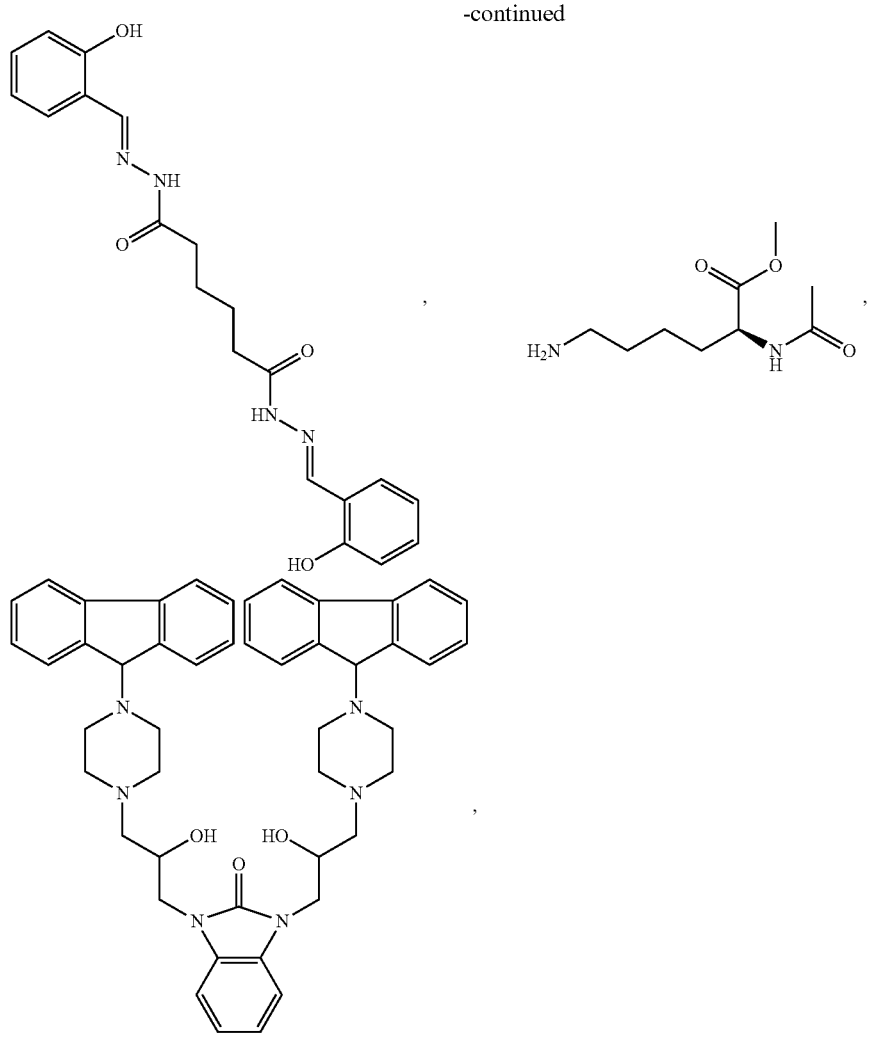

or pharmaceutically acceptable salts thereof.

Candidate compounds screened include chemical compounds. In some aspects, the candidate compound is a small organic molecule having a molecular weight of more than about 50 and less than about 2,500 daltons. Compounds screened are also found among biomolecules including, but not limited to: peptides, saccharides, fatty acids, steroids, pheromones, purines, pyrimidines, derivatives, structural analogs or combinations thereof. The compounds screened can include functional groups necessary for structural interaction with proteins, particularly hydrogen bonding, and typically include at least an amine, carbonyl, hydroxyl, or carboxyl group.

Candidate compounds can be obtained from a wide variety of sources including libraries of synthetic or natural compounds. Compounds to be screened can be produced, for example, by bacteria, yeast or other organisms (e.g., natural products), produced chemically (e.g., small molecules, including peptidomimetics), or produced recombinantly. It is further contemplated that natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

In many drug screening programs, with test libraries of compounds and natural extracts, high throughput assays are desirable in order to maximize the number of compounds surveyed in a given period of time. Assays of described herein may be developed with purified or semi-purified proteins or with lysates. These assays are often preferred as "primary" screens in that they can be generated to permit rapid development and relatively easy detection of an alteration in a molecular target, which is mediated by a test agent.

Assays described herein can include cell-based assays. Cell-based assays may be performed as either a primary screen, or as a secondary screen to confirm the activity of compounds identified in a cell free screen, such as an in silico screen.

Embodiments described herein also relate to a method of screening in silico for a compound effective as an RRAmod. For example, a 3-D model of the hexamer interface epitope of RR1 targeted by small molecules can be used to provide a pharmacophore using X-ray Crystallography. An initial model can then be generated using a suitable protein modeling software program. In some aspects, the model can then be subjected to energy refinement with a software program such as SURFLEX dock. The pharmacophore can be modified to comply to the Lipinski limits to design drug-like molecules with good bioavailability. In one embodiment, the template used for docking was the hexamer interface of ribonucleotide reductase as shown in FIG. 1.

Once a model is built, small molecule RRAmods that bind to ribonucleotide reductase at the hexamer interface of RR1 can be identified by methods well known in the relevant art using in silico conformation screening techniques. For example, virtual screening of the University of Cincinnati Drug Discovery Center (UC DCC) Library of 350,000 compounds can be performed using the drug discovery software SYBYLX1.3 (Tripos, St. Louis, Mo.). Such software can also be used to design modified analogs of compounds for use as RRAmods. In parallel, ZINC and other commercial databases can be searched using within SYBYLX1.3 software for lead compounds that satisfy the pharmacophore. These hits can be docked and scored using SURFLEX dock option in SYBYLX1.3. The best hits can then be discriminated using two scoring functions called, a docking score and the C-score. The docking score is theoretically equivalent to the negative logarithm of $K_d$, while C-score is a consensus scoring function. Hence, docking scores that are equal to 6 would mean a theoretical $K_d$ of micromolar. The maximum C-score that can be obtained is five. Based on these criteria, after virtually screening the library, the best scoring candidates can be selected and then tested using various in vitro and cell based assays described herein and known in the art for efficacy. The larger numbers obtained for dock score and C-scores greater than 6 and 4-5 respectively represents the high ranking inhibitors that are predicted to have high affinities.

In some aspects, about 20,000 compounds can be selected from in silico screening for an in vitro high-throughput screening (HTS). HTS can be carried out using an automated HTS system which performs biochemical and cell-based assays using 96 or 384-well microtiter plates. The system includes detectors, $CO_2$ incubators, pipetting systems, a plate washer, centrifuge, a storage unit, bar code readers, xyz robots, turntables, and pushers necessary for fully automated screening. A Jobin Yvon-Spex fluorescence spectrophotometer can be used to record the spectra. Alternatively, a multimode PERKIN-ELMER plate reader can be used for detecting fluorescence intensity, fluorescence polarization, fluorescence resonance energy transfer, luminescence, or absorbance using ZEISS optics and a sensitive CCD camera. The PERKIN-ELMER Opera detector performs high content screening using confocal microscopy and image analysis software powered by onboard servers. Lasers and CCD cameras allow measurement of subcellular localization, binding events or any other microscopic images which can be rapidly quantitated. Image analysis is performed immediately after the image is captured and stored in a database. All other data can be analyzed using GENEDATA HTS analysis software (Switzerland), stored in a GENEDATA database based on ORACLE.

Figure 12:
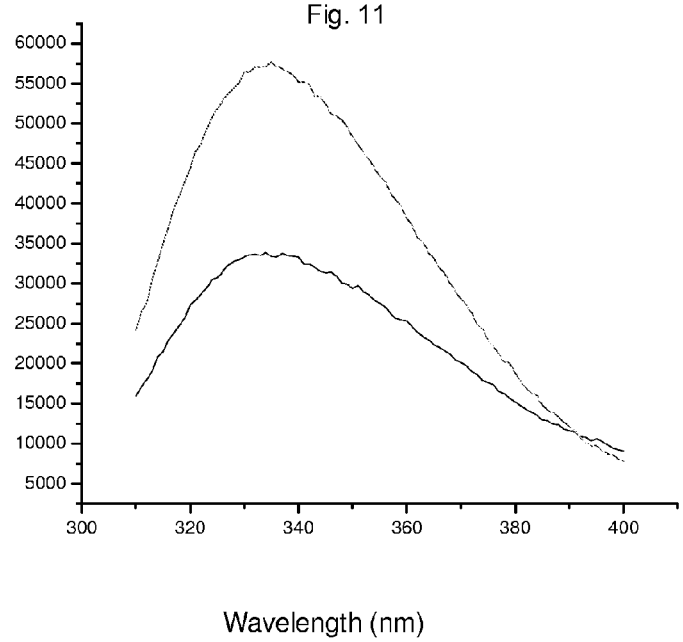
FIG. 12 is a graph illustrating the tryptophan fluorescence spectra of HurI (Human ribonucleotide reductase) and HurI in the presence of Drug 4.

In some embodiments, in vitro HTS includes a fluorescence based assay adapted for HTS. For example, in vitro HTS can employ tryptophan fluorescence quenching. The binding sites of proteins are known to often contain tryptophan (Trp) residues, whose fluorescent properties may be altered upon ligand binding. Conformational changes within the binding site or simply the presence of the ligand can result in either fluorescence quenching or enhancement, which may be utilized to quantitatively investigate protein-ligand interactions. Change in intrinsic tryptophan fluorescence is used to measure the binding of a candidate agent to the Sml1 binding site of ribonucleotide reductase. As shown in the Example below and in FIG. 12, the trytophan fluorescence spectra of Hurl (Human ribonucleotide reductase) and a candidate compound can be recorded and then compared in order to determine the extent of quenching. The ribonucleotide reductase samples are titrated with 65 µM candidate compounds at room temperature where a decrease in fluorescence, or quenching, can be correlated with the binding affinity of the candidate compound to the Sml1 binding site of ribonucleotide reductase and/or a conformational change in the ribonucleotide reductase Sml1 binding site.

In some aspects, candidate RRAmod compounds, including those collected from an in silico similarity search or HTS assay, may be further screened for efficacy using in vitro and/or in vivo experimental screening methods known in the art. The efficacy of an identified compound can be assessed by generating dose response curves from data obtained using various concentrations of the test compound. Moreover, a control assay can also be performed to provide a baseline for comparison. Such candidates can be further tested for their effects on cancer and tumor cell growth, proliferation, apoptosis, differentiation, and transformation properties compared to controls as well as their ability to inhibit de novo DNA synthesis in vitro; unbalance nucleotide pool of DNA precursor molecules in vitro; modulate ribonucleotide reductase activity in vitro; and/or for other properties, such as the ability to inhibit cell growth and increase the toxicity of neoplastic cells in vivo.

In some embodiments, assays used for in vitro screening of candidate compounds for cell growth inhibition can include DNA synthesis assays and MTT colorimetric assays to measure cell metabolism. For example, a DNA synthesis assay can include the steps of: (a) contacting the neoplastic cell with various concentrations of a candidate compound; and (b) comparing the DNA synthesis of the cell in step (a) with the DNA synthesis of the cell in the absence of the compound so as to determine whether the compound significantly inhibits ribonucleotide reductase activity, thereby reducing the growth of the cell. One can also determine the $IC_{50}$ of a candidate compound if the compound is found to significantly inhibit ribonucleotide reductase activity. The $IC_{50}$ of a drug can be determined by constructing a dose-response curve and examining the effect of different concentrations of a candidate agent on cell growth and/or ribonucleotide reductase enzyme activity. $IC_{50}$ values can be calculated for a given compound by determining the concentration needed to inhibit half of the maximum biological response of the compound.

For in vivo screening of candidate compounds, the candidate compound can be administered in any manner desired and/or appropriate for delivery of the compound in order to affect a desired result. For example, the candidate compound can be administered to a mammalian subject by injection (e.g., by injection intravenously, intramuscularly, subcutaneously, or directly into the tissue in which the desired affect is to be achieved), topically, orally, or by any other desirable means.

Normally, this screen will involve a number of animals receiving varying amounts and concentrations of the candidate compounds (from no compound to an amount of compound that approaches an upper limit of the amount that can be delivered successfully to the animal), and may include delivery of the compound in different formulations. The compounds can be administered singly or can be combined in combinations of two or more, especially where administration of a combination of compounds may result in a synergistic effect.

The effect of compound administration upon the animal model can be monitored by any suitable method such as assessing the number and size of tumors, overall health, survival rate, etc. A candidate compound is identified as an effective compound for use in the treatment of a neoplastic disorder in a subject where candidate compound inhibits neoplastic cell growth in the animal in a desirable manner (e.g., by binding to the Sml1 allosteric binding site of ribonucleotide reductase and allosterically inhibiting the enzyme's activity, etc.). In some aspects, effective compounds can be identified as having low toxicity in vivo.

As shown in the Examples below, RRAmods disclosed herein have been shown to bind to the hexamer interface of RR1 and inhibit growth of multiple cancer cell types in vitro, supporting the use of these RRAmods to treat a wide range of neoplastic diseases and disorders. Thus, in accordance with another embodiments, RRAmods described herein can be used for the preparation of a pharmaceutical composition for the treatment of a neoplastic disorder in a subject. In one embodiment, the subject is suffering from a neoplastic disorder characterized by increased cell growth. In another embodiment, the subject is suffering from cancer.

A therapeutically effective amount of a RRAmod described herein can be administered to a subject for the treatment of a variety of conditions in order to inhibit cell growth in the subject. Such conditions include, without being limited thereto, neoplastic disorder, and in particular all types of solid tumors; skin proliferative diseases (e.g., psoriasis); and a variety of benign hyperplasic disorders.

In one aspect, the neoplastic disorder is cancer. The cancer can include, but is not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, meningoma, medulloblastoma, schwannoma and epidymoma. In certain aspects, the cancer is a pancreatic, breast, lung, colon or glyoblastoma cancer.

In another aspect, the neoplastic disorder is a solid tumor. Exemplary solid tumors include carcinomas, sarcomas, adenomas, and cancers of neuronal origin and if fact to any type of cancer which does not originate from the hematopoeitic cells and in particular concerns: carcinoma, sarcoma, adenoma, hepatocellular carcinoma, hepatocellularcarcinoma, hepatoblastoma, rhabdomyosarcoma, esophageal carcinoma, thyroid carcinoma, ganglioblastoma, fibrosarcoma, myxosarcoma, liposarcoma, cohndrosarcoma, osteogenic sarcoma, chordoma, angiosarcoma, endotheliosarcoma, lymphagiosarcoma, synovioama, Ewing's tumor, leimyosarcoma, rhabdotheliosarcoma, colon carcinoma, pancreatic cancer, breast cancer, ovarian cancer, prostate cancer, squamous cell carcinoma, basal cell carcinoma, adenocarcinoma, renal cell carcinoma, hematoma, bile duct carcinoma, melanoma, choriocarcinoma, seminoma, embryonal carcinoma, Wilms' tumor, cervical cancer, testicular tumor, lung carcinoma, small lung carcinoma, bladder carcinoma, epithelial carcinoma, glioma, astrocyoma, medulloblastoma, craniopharyngioma, ependynoma, pinealoma, retinoblastoma, multiple myeloma, rectal carcinoma, thyroid cancer, head and neck cancer, brain cancer, cancer of the peripheral nervous system, cancer of the central nervous system, neuroblastoma, cancer of the endometrium, as well as metastasis of all the above.

Benign hyperplasic disorders include, without being limited thereto, benign prostate hyperplasia (BPH), non-tumorigenic polyps in the digestive tract, in the uterus and others.

In addition to cancer, the RRAmods disclosed herein may be used to treat other conditions associated with aberrant ribonucleotide reductase enzyme activity such as for example various mitochondrial, redox-related, degenerative diseases, and viruses such as HIV.

When used as therapeutic agents in the treatment of neoplastic disorders, the RRAmods can be conveniently formulated into pharmaceutical formulations composed of one or more of the compounds (e.g., RRAmods of formulas (I-III) or an RRAmodidentified by a screening assay as described above) in association with a pharmaceutically acceptable carrier or excipient. (See Remington: The Science and Practice of Pharmacy (Gennaro ed. 22nd Edition, Pharmaceutical Press, London, UK, 2012), which discloses typical carriers and conventional methods of preparing pharmaceutical formulations).

In making the compositions, the RRAmod is usually mixed with the excipient, diluted by an excipient or enclosed within a carrier which can be in the form of a capsule, sachet, paper or other container. When the excipient serves as a diluent, it can be a solid, semi-solid, or liquid material, which acts as a vehicle, carrier or medium for the RRAmod. Thus, the compositions can be in the form of tablets, pills, powders, lozenges, sachets, cachets, elixirs, suspensions, emulsions, solutions, syrups, aerosols (as a solid or in a liquid medium), soft and hard gelatin capsules, suppositories, sterile injectable solutions, and sterile packaged powders. The RRAmods can also be administered to a subject as a stabilized prodrug to increase the activity, bioavailability, stability or otherwise alter the properties of the RRAmod.

The effective amount of RRAmod in the pharmaceutical composition and unit dosage form thereof may be varied or adjusted widely depending upon the particular application, the manner or introduction, the potency of the particular compound, and the desired concentration.

The effective amount is typically determined in appropriately designed clinical trials (dose range studies) and the person versed in the art will know how to properly conduct such trials in order to determine the effective amount. As generally known, an effective amount depends on a variety of factors including the affinity of the RRAmod to the allosteric Sml1 binding site, its distribution profile within the body, a variety of pharmacological parameters such as half life in the body, on undesired side effects, if any, on factors such as age and gender, etc.

The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In this case, the composition will typically be administered over an extended period of time in a single daily dose, in several doses a day, as a single dose and in several days, etc. The treatment period will generally have a length proportional to the length of the disease process and the specific RRAmod effectiveness and the patient species being treated.

RRAmods and pharmaceutical compositions thereof can be administered to the subject by any suitable means, including, for example, oral, intravenous, intramuscular, intra-arterial, subcutaneous, intranasal, via the lungs (inhalation) and through local administration.

RRAmods described herein can be used as single agents or in combination or in conjunction with one or more other therapeutic agents in the treatment of the aforementioned diseases, disorders and conditions for which RRAmods or the other agents have utility. In some embodiments, a combination of an RRAmod and other therapeutic agent together is safer or more effective than either drug alone.

In some embodiments, the other therapeutic agent used in a combination therapy can include at least one anti-proliferative agent selected from the group consisting at least one of a chemotherapeutic agent, an anticancer agent, an antimetabolite, a DNA damaging agent, an antitumorgenic agent, an antimitotic agent, an antiviral agent, an antineoplastic agent, an immunotherapeutic agent, and a radiotherapeutic agent. Additional therapeutic agents used in combination therapies with RRAmods can include biguanides (e.g., metformin, phenformin and buformin), AP endonuclease inhibitors (e.g., methoxyamine (MX)), BER inhibitors including PARP inhibitors, and ribonucleotide reductase inhibiting agents. Exemplary ribonucleotide reductase inhibiting agents for use in conjunction with RRAmods include $O^6$-methyl-arabinofuranosyl guanine (nelarabine), 2'-fluoro-2'-deoxyarabinofuranosyl-2-chloroadenine (clofarabine), $N^4$-pentyloxycarbonyl-5'-deoxy-5-fluorocytidine (capecitabine), 2,2-difluoro-2'-deoxyadenosine (cladribine), arabinofuranosyl-2-fluoroadenine (fludarabine), 2'-deoxycoformycin (pentostatin), 5-fluoro-2'deoxyuridine, arabinofuranosylcytosine (cytarabine), 6-thioguanine, 5-fluorouracil, methotrexate, 6-mercaptopurine.

In some aspects, RRAmods can be used in a combination therapy with an anti-proliferative agent. The phrase "anti-proliferative agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development, which can be included by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, anti-metastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endotheliai cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

A first family of anti-proliferative agents, which may be used in combination therapy with an RRAmod consists of antimetabolite-type anti-proliferative agents. Antimetabolites are typically reversible or irreversible enzyme inhibitors, or compounds that otherwise interfere with the replication, translation or transcription of nucleic acids. Examples of antimetabolite antineoplastic agents that may be used include, but are not limited to acanthifolic acid, aminothiadiazole, anastrozole, bicalutamide, brequinar sodium, capecitabine, carmofur, Ciba-Geigy CGP-30694, cladribine, cyclopentyl cytosine, cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, finasteride, floxuridine, fludarabine phosphate, N-(2'-furanidyl)-5-fluorouracil, Daiichi Seiyaku FO-152, fluorouracil (5-FU), 5-FU-fibrinogen, gemcitabine, isopropyl pyrrolizine, Lilly LY-188011, Lilly LY-264618, methobenzaprim, methotrexate, Wellcome MZPES, nafarelin, norspermidine, nolvadex, NCI NSC-127716, NCI NSC-264880, NCI NSC-39661, NCI NSC-612567, Warner-Lambert PALA, pentostatin, piritrexim, plicamycin, Asahi Chemical PL-AC, stearate; Takeda TAC-788, thioguanine, tiazofurin, Erbamont TIF, trimetrexate, tyrosine kinase inhibitors, tyrosine protein kinase inhibitors, Taiho UFT, toremifene, and uricytin, all of which are disclosed in U.S. Pat. No. 6,916,800, which is herein incorporated by reference in its entirety.

A second family of anti-proliferative agents, which may be used in combination therapy with the RRAmods, consists of alkylating-type anti-proliferative agents. The alkylating agents are believed to act by alkylating and cross-linking guanine and possibly other bases in DNA, arresting cell division. Typical alkylating agents include nitrogen mustards, ethyleneimine compounds, alkyl sulfates, cisplatin, and various nitrosoureas. A disadvantage with these compounds is that they not only attack malignant cells, but also other cells which are naturally dividing, such as those of bone marrow, skin, gastro-intestinal mucosa, and fetal tissue. Examples of alkylating-type anti-proliferative agents that may be used include, but are not limited to, Shionogi 254-S, aldo-phosphamide analogues, altretamine, anaxirone, Boehringer Mannheim BBR-2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr)$_2$, diphenylspiromustine, diplatinum cytostatic, Erba distamycin derivatives, Chugai DWA-2114R, ITI E09, elmustine, Erbamont FCE-24517, estramustine phosphate sodium, etoposide phosphate, fotemustine, Unimed G-6-M, Chinoin GYKI-17230, hepsulfam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromus-tine, Tanabe Seiyaku TA-077, tauromustine, temozolomide (TMZ), teroxirone, tetraplatin and trimelamol.

A third family of anti-proliferative agents that may be used in combination therapy with the RRAmods consists of antibiotic-type anti-proliferative agents. Examples of antibiotic-type anti-proliferative agents that may be used include, but are not limited to Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of anti-proliferative agents that may be used in combination therapy with the RRAmods consists of synthetic nucleosides. Several synthetic nucleosides have been identified that exhibit anticancer activity. A well known nucleoside derivative with strong anticancer activity is 5-fluorouracil (5-FU). 5-Fluorouracil has been used clinically in the treatment of malignant tumors, including, for example, carcinomas, sarcomas, skin cancer, cancer of the digestive organs, and breast cancer. 5-Fluorouracil, however, causes serious adverse reactions such as nausea, alopecia, diarrhea, stomatitis, leukocytic thrombocytopenia, anorexia, pigmentation, and edema. Derivatives of 5-fluorouracil with anti-cancer activity have been described in U.S. Pat. No. 4,336,381, which is herein incorporated by reference in its entirety. Further 5-FU derivatives have been described in the following patents listed in JP 50-50383, JP 50-50384, JP 50-64281, JP 51-146482, and JP 53-84981 hereby individually incorporated by reference herein. Further synthetic nucleoside analogs include 4-amino-1-(2-deoxy-b-D-erythro-pentofuranosyl)-1,3,5-triazin-2(1H)-one (e.g., 5-aza-21-deoxycytidine, decitabine, or DACOGEN, Eisai Inc., Woodcliff Lake, N.J.). Other examples, of nucleoside analogs that can be used to treat cancer are listed in U.S. Pat. No. 4,000,137, which is incorporated herein by reference, Cytosine arabinoside (also referred to as Cytarabin, araC, and Cytosar) and 5-Azacytidine (VIDAZA, Celegene Corp., Summit, N.J.).

A fifth family of anti-proliferative agents that may be used in combination therapy with the RRAmods consists of hormonal agents. Examples of hormonal-type anti-proliferative agents that may be used include, but are not limited to Abarelix; Abbott A-84861; Abiraterone acetate; Aminoglutethimide; anastrozole; Asta Medica AN-207; Antide; Chugai AG-041R; Avorelin; aseranox; Sensus B2036-PEG; Bicalutamide; buserelin; BTG CB-7598; BTG CB-7630; Casodex; cetrolix; clastroban; clodronate disodium; Cosudex; Rotta Research CR-1505; cytadren; crinone; deslorelin; droloxifene; dutasteride; Elimina; Laval University EM-800; Laval University EM-652; epitiostanol; episteride; Mediolanum EP-23904; EntreMed 2-ME; exemestane; fadrozole; finasteride; flutamide; formestane; Pharmacia & Upjohn FCE-24304; ganirelix; goserelin; Shire gonadorelin agonist; Glaxo Wellcome GW-5638; Hoechst Marion Roussel Hoe-766; NCI hCG; idoxifene; isocordoin; Zeneca ICI-182780; Zeneca ICI-118630; Tulane University J015X; Schering Ag J96; ketanserin; lanreotide; Milkhaus LDI-200; letrozol; leuprolide; leuprorelin; liarozole; lisuride hydrogen maleate; loxiglumide; mepitiostane; Leuprorelin; Ligand Pharmaceuticals LG-1127; LG-1447; LG-2293; LG-2527; LG-2716; Bone Care International LR-103; Lilly LY-326315; Lilly LY-353381-HCl; Lilly LY-326391; Lilly LY-353381; Lilly LY-357489; miproxifene phosphate; Orion Pharma MPV-2213ad; Tulane University MZ-4-71; nafarelin; nilutamide; Snow Brand NKS01; octreotide; Azko Nobel ORG-31710; Azko Nobel ORG-31806; orimeten; orimetene; orimetine; ormeloxifene; osaterone; Smithkline Beecham SKB-105657; Tokyo University OSW-1; Peptech PTL-03001; Pharmacia & Upjohn PNU-156765; quinagolide; ramorelix; Raloxifene; statin; sandostatin LAR; Shionogi S-10364; Novartis SMT-487; somavert; somatostatin; tamoxifen; tamoxifen methiodide; teverelix; toremifene; triptorelin; TT-232; vapreotide; vorozole; Yamanouchi YM-116; Yamanouchi YM-511; Yamanouchi YM-55208; Yamanouchi YM-53789; Schering AG ZK-1911703; Schering AG ZK-230211; and Zeneca ZD-182780.

A sixth family of anti-proliferative agents that may be used in combination therapy with the RRAmods consists of a miscellaneous family of antineoplastic agents including, but not limited to alpha-carotene, alpha-difluoromethylarginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristo-Myers BMY-40481, Vestar boron-10, bromofosfamide, Wellcome BW 502, Wellcome BW-773, calcium carbonate, Calcet, Calci-Chew, Calci-Mix, Roxane calcium carbonate tablets, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Cell Pathways CP-461, Yakult Honsha CPT-11, crisnatol, curaderm, cytochalasin B, cytarabine, cytocytin, Merz D-609, DABIS maleate, dacarbazine, datelliptinium, DFMO, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel, Encore Pharmaceuticals E7869, elliprabin, elliptinium acetate, Tsumura EPMTC, ergotamine, etoposide, etretinate, Eulexin®, Cell Pathways Exisulind® (sulindac sulphone or CP-246), fenretinide, Merck Research Labs Finasteride, Florical, Fujisawa FR-57704, gallium nitrate, gemcitabine, genkwadaphnin, Gerimed, Chugai GLA-43, Glaxo GR 63178, grifolan NMF-5N, hexadecylphosphocholine, Green Cross HO-221, homoharringtonine, hydroxyurea, BTG ICRF-187, ilmofosine, irinotecan, isoglutamine, isotretinoin, Otsuka JI-36, Ramot K 477, ketoconazole, Otsuak K-76COONa, Kureha Chemical K-AM, MECT Corp KI-8110, American Cyanamid L-623, leucovorin, levamisole, leukoregulin, lonidamine, Lundbeck LU-23-112, Lilly LY 186641, Materna, NCI (US) MAP, marycin, Merrel Dow MDL-27048, Medco MEDR-340, megestrol, merbarone, merocyanine derivatives, methylanilinoacridine, Molecular Genetics MGI-136, minactivin, mitonafide, mitoquidone, Monocal, mopidamol, motretinide, Zenyaku Kogyo MST-16, Mylanta, N (retinoyl)amino acids, Nilandron; Nisshin Flour Milling N-021, N-acylated-dehydroalanines, nafazatrom, Taisho NCU-190, Nephro-Calci tablets, nocodazole derivative, Normosang, NCI NSC-145813, NCI NSC-361456, NCI NSC-604782, NCI NSC-95580, octreotide, Ono ONO-112, oquizanocine, Akzo Org 10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, retinoids, Encore Pharmaceuticals R-flurbiprofen, Sandostatin; Sapporo Breweries RBS, restrictin-P, retelliptine, retinoic acid, Rhone-Poulenc RP-49532, Rhone-Poulenc RP-56976, Scherring-Plough SC-57050, Scherring-Plough SC-57068, seienium (selenite and selenomethionine), SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, Sugen SU-101, Sugen SU-5416, Sugen SU-6668, sulindac, sulindac sulfone; superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine, vinblastine sulfate, vincristine, vindesine, vinestramide, vinorelbine, vintriptol, vinzolidine, withanolides, Yamanouchi YM-534, Zileuton, ursodeoxycholic acid, and Zanosar.

In the instances of combination therapies described herein, it will be understood the administration further includes a pharmaceutically or therapeutically effective amount of the additional therapeutic agent in question. The second or additional therapeutic agents described herein may be administered in the doses and regimens known in the art or may be administered in low doses.

In some embodiments, the administration of a RRAmod and an additional therapeutic agent can result in a synergistic effect. A "synergistic effect" as used herein means the combined effect of two or more therapeutic agents can be greater than the sum of the separate effects of the agents alone. For example, the combined effect of a RRAmod, and an anticancer agent, such as metformin, can be greater than the sum of the separate effects of an RRAmod and metformin alone.

Where the combined effect of administering a RRAmod and another therapeutic agent is greater than the sum of the separate effects of the RRAmod and the other agent alone, the RRAmod and/or therapeutic agent can be administered to the subject in a lower dose or even a sub-therapeutic dose. A benefit of lowering the dose of the combination therapeutic agents and therapies can include a decrease in the incidence of adverse effects associated with higher dosages. For example, by the lowering the dosage of a chemotherapeutic agent such as methotrexate, a reduction in the frequency and the severity of nausea and vomiting will result when compared to that observed at higher dosages.

The additional therapeutic agent can be administered by a route and in an amount commonly used therefore, contemporaneously or sequentially with a RRAmod compound. When administered as a combination, a RRAmod compound and additional therapeutic agent(s) can be formulated as separate compositions which are given at the same time or different times, or the therapeutic agents can be given as a single composition.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention Example 1

Allosteric Modulators of Ribonucleotide Reductase (RR1)

Hexamer Interface of RR1

Until now, the modulation of RR activity by small molecules binding at the hexamer interface was unknown. Using X-ray Crystallography, we have mapped out a new druggable site of ribonucleotide reductase bound by potent protein inhibitor small molecules that modulates its activity. We have discovered the epitope targeted by allosteric effectors on the large subunit of ribonucleotide reductase. The epitope includes residues 1 to 21 of the N terminus of ribonucleotide reductase I bearing the sequence MHVIKRDGRQERVMFDKITSR (SEQ ID NO:1). However, the sequence also includes residues 1 to 30.

Our discovery shows that small molecules will bind this region and allosterically modulate the enzyme. Moreover, small molecules inhibit the ribonucleotide reductase hexamer formation.

Screening for RR Allosteric Inhibitors (RRAmods)

Using the Cincinnati chemical library and fluorescence-based assays adapted for HTS we conducted a high throughput screen (HTS) for small molecules that will bind at the hexamer interface of human RR1 and modulate ribonucleotide reductase enzyme activity.

in Silico Virtual Screening

We conducted an in silico virtual screening of the Cincinnati library using the drug discovery software SYBYLX1.3. Here, the library was subject to docking of ligands using the SUFFLEX dock option in SYBYL. The best hits were discriminated using two scoring functions called, a docking score and the C-score. The docking score is theoretically equivalent to the negative logarithm of $K_d$, while C-score is a consensus scoring function. Hence, docking scores that equal to 6 would mean a theoretical $K_d$ of micromolar. The maximum C-score that can be obtained is five. Based on these criteria, after virtually screening the library, the best 250 hits were chosen. The template used for docking was the hexamer interface of RR1 reported by us in Fairman, et al. 2011, Nat. Struc. Mol. Biol. (see FIG. 1).

Tryptophan Fluorescence Quenching Assay

We established fluorescence-based assays where fluorescence quenching occurs upon small molecules binding at the hexamer interface of RR1. We screened the top 100 hits from the virtual screen using a trytophan fluorescence-based quenching assay.

Methods

We recorded the tryptophan fluorescence spectra of Hur1 (Human ribonucleotide reductase) and Hur1 in the presence of Drug 4. The spectra were recorded using a Jobin-Yvon-Spex fluorescence spectrophotometer by exciting the sample at a wavelength of 295 nm. The samples were titrated with 65 µM of Drug 4 at RT. Extent of quenching was determined after correcting for the compound fluorescence in the same buffer.

Results

Of the first 10 compounds to be tested, we have obtained 11 hits. Some of these candidate compounds achieved as much as 40-50% fluorescence quenching (See FIG. 12). We also observed that some of the compounds induce a blueshift in the wavelength indicating the promotion of hydrophobic interactions leading to a possible tightening of the structure.

DNA Synthesis Assay

In order to determine the relative activity of candidate drugs and an estimate of the general range where the IC50s would fall, we exposed candidate compounds for 2 continuous days. The results are summarized in Table 1 below:

TABLE 1

| DRUG ID | ACTIVITY | $IC_{50}$ |
|---|---|---|
| Drug 1 | most potent | $IC_{50}$ ~1 µM or less |
| Drug 2 | $2^{nd}$ most potent | $IC_{50}$ ~1-5 µm |
| Drug 3 | little or no activity at 100 µM | null |
| Drug 4 | a bit of activity | $IC_{50}$ near 50-100 µm |

MTT Assay I

We conducted an MTT assay to measure cell metabolism as a surrogate for cell number using A549, Non-Small Cell Lung cells; 231, Triple negative breast cells; and LN229. All values are relative to untreated controls, corrected for any MTT absorbance due to media alone.

Method

The cells were treated with continuous doses of the indicated drugs for three days, at which time the MTT assay was run. The control is listed as a dose of 0.1 uM because we plot on a log scale and wish to avoid taking the log of 0 in the calculations.

The results are shown in FIGS. 2-8 and summarized below in Table 2.

TABLE 2

| DRUG ID | ACTIVITY | $IC_{50}$ |
|---|---|---|
| Drug 1 | Steady effect on all three cell lines | $IC_{50}$s in the 0.8-2.0 µM range |
| Drug 2 | Shows an extremely dramatic effect. Visually the cells have undergone either necrosis or apoptosis, and few intact cells are evident once they hit their respective toxic dose | $IC_{50}$ between 3-12 uM |
| Drug 3 | virtually without effect, even at 100 µM | null |
| Drug 4 | some toxicity at 100 µM, but little or none at 50 uM | null |

MTT Assay II

Figure 9:
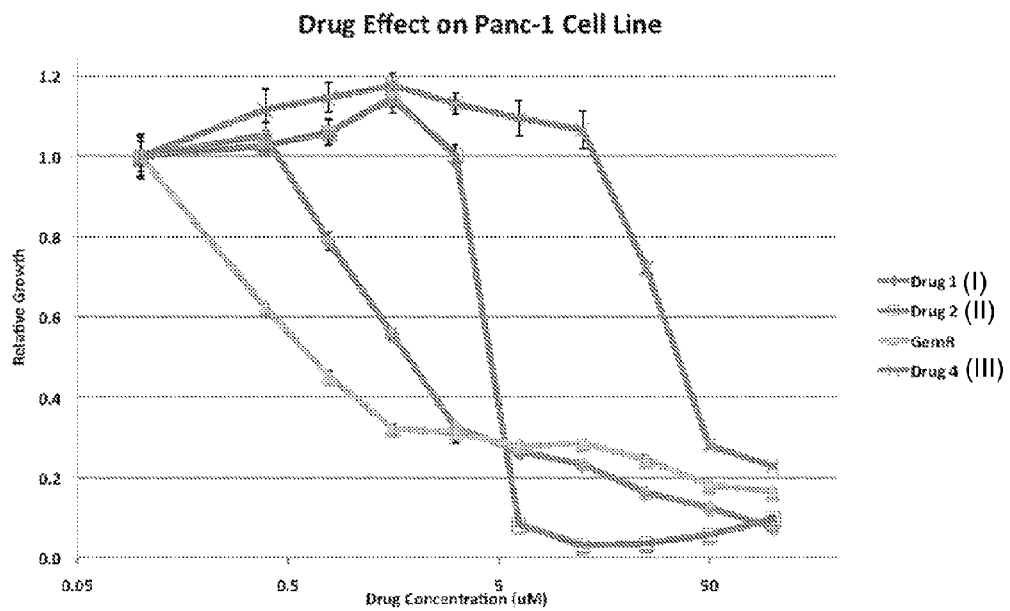
FIG. 9 is a graph showing the drug effects of Drug 1, Drug 2, Drug 4 and Gemcitabine on the Panc-1 pancreatic cell line.
Figure 10:
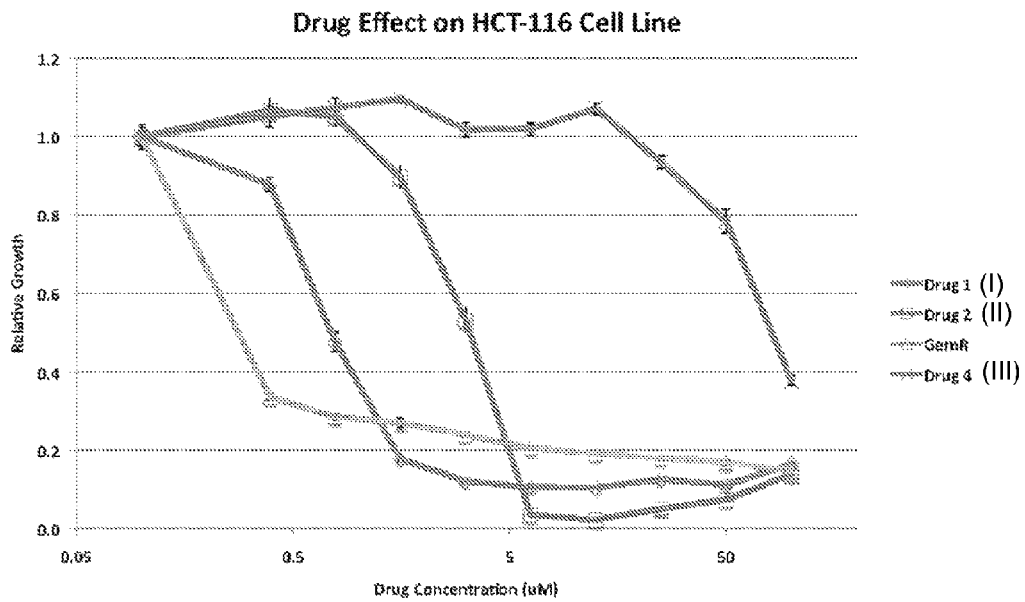
FIG. 10 is a graph showing the drug effects of Drug 1, Drug 2, Drug 4 and Gemcitabine on the HCT-116 colon cell line.
Figure 11:
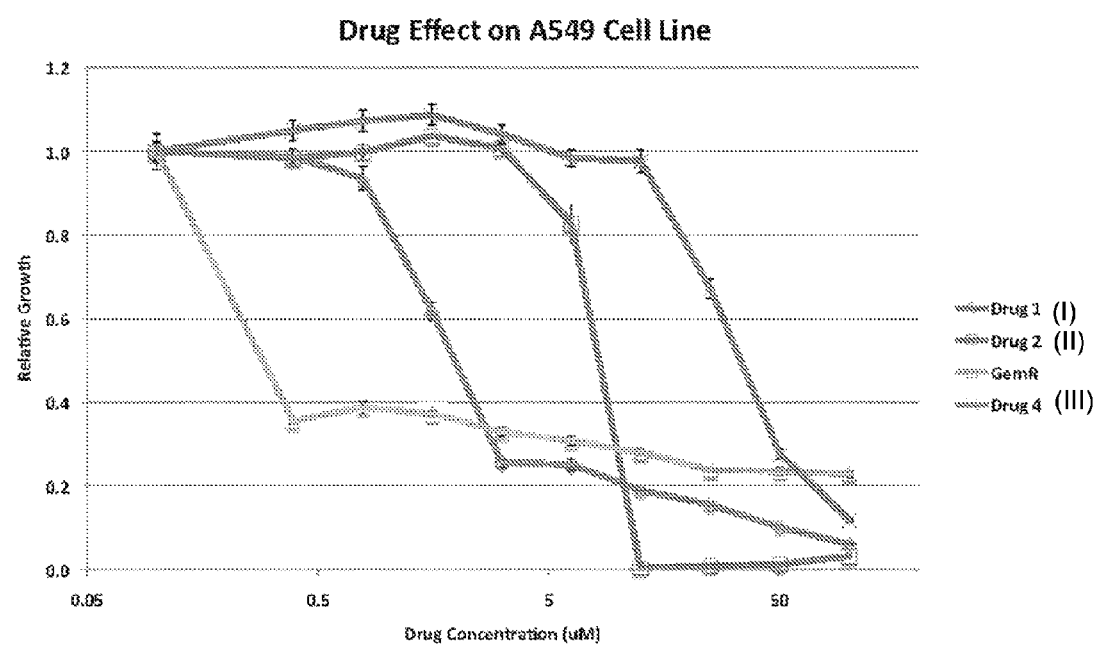
FIG. 11 is a graph showing the drug effects of Drug 1, Drug 2, Drug 4 and Gemcitabine on the A549 non-small lung cell line.

We conducted an MTT assay to measure cell metabolism as a surrogate for cell number using A549, Non-Small Cell Lung cells; pancreatic cells (Panc-1); and colon cells (HCT-116). The results for Drugs I-III are shown in FIGS. 9-11 and summarized in Table 3 below. In addition Gemcitabien $IC_{50}$s were found to be between 100 nm-500 nm

TABLE 3

| Drug # | Batch | GRI | Compound | Weight | Docking Score | $IC_{50}$ (µM) |
|---|---|---|---|---|---|---|
| 1 | 140247 | 253941 | | 538 | 8.27 | 0.6-2 |
| 2 | 220435 | 193840 | | 722 | 7.52 | 3-8 |

TABLE 3-continued

| Drug # | Batch | GRI | Compound | Weight | Docking Score | IC$_{50}$ (μM) |
|---|---|---|---|---|---|---|
| 4 | 528949 | 258256 | 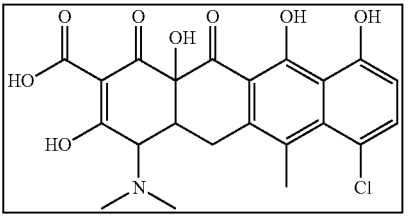 [SMILES: Cc1c2c(c(O)c3c(O)ccc(Cl)c13)C(=O)C1(O)C(=O)C(C(=O)O)=C(O)C(N(C)C)C1C2] | 460 | 7.2 | 30-70 |

Example 2

Figure 13:
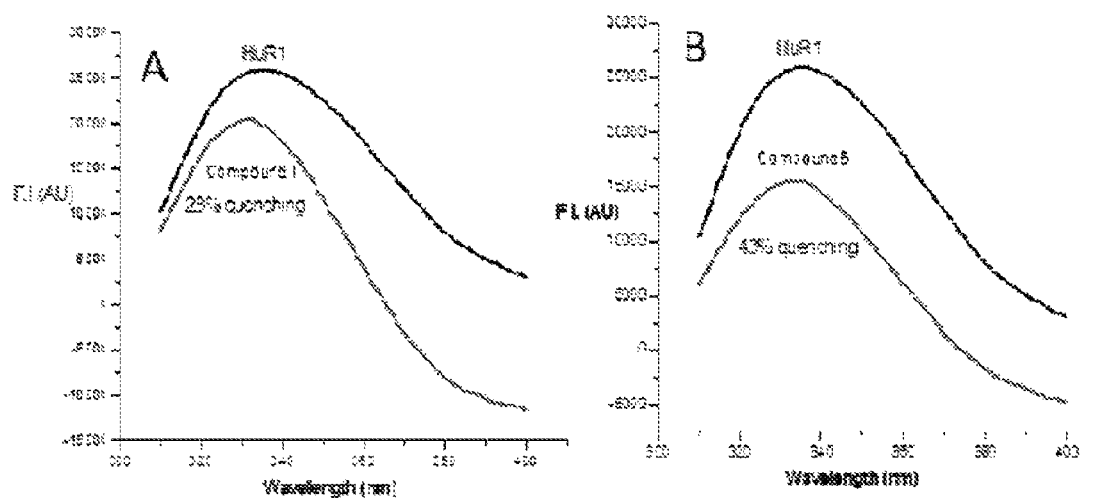
FIG. 13 illustrates a compound 2 increases cytotoxicity of gemcitabine of cis-platin. Growth inhibition studies on MDA-MB-231 human breast carcinoma cell line in the presence of gemcitabine (F2CDP-red) or cis-platin (CDDP-blue) alone (solid lines), or in combination with a non-toxic does of compound 2 (dashed lines).
Figure 14:
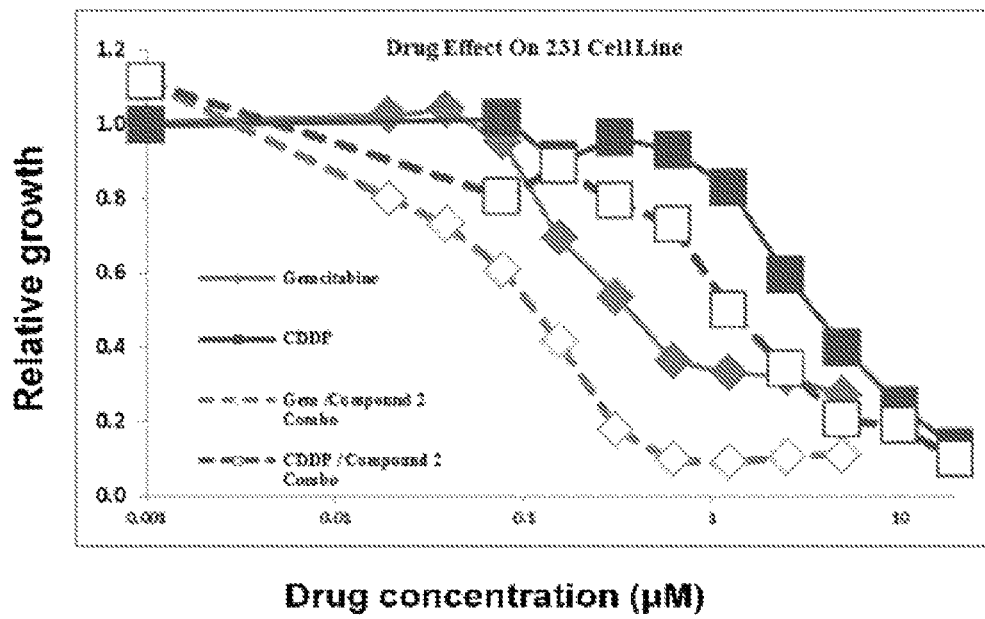
FIG. 14 illustrates that compound 3 is cytotoxic against human breast carcinoma cells. Growth of the MDA-MB-231 cancer cell line is inhibited by compound 3.
Figure 15:
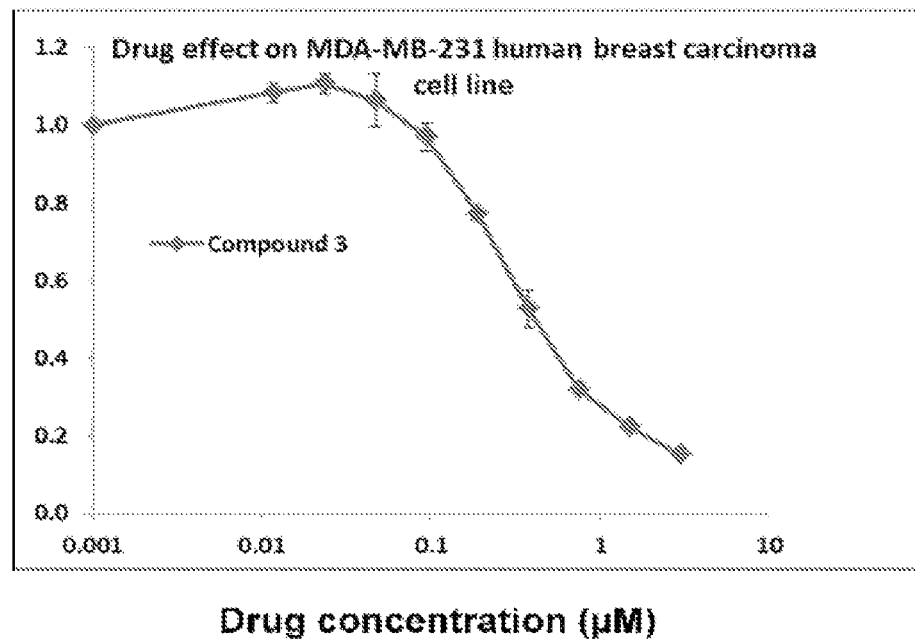

We conducted a high throughput screen using the Cincinnati drug library (the former Proctor and Gamble drug library). We used a multidisciplinary screening approach as follows. (1) We used in silico docking experiments with the N-terminus of hRRM1 to discover small molecule ligands (2) We tested the highest-ranking hits for hRRM1 binding using a fluorescence quenching assay (FIG. 13) (3) We tested the ligands that bound to hRRM1 in cell culture experiments to assess their ability to kill cancer cell lines (FIGS. 14 and 15), (4) the ligands that demonstrated anticancer properties for RR inhibition (Table 4) and (5). Finally, we attempted to co-crystallize RR with the ligands or soak them into hRRM1 crystals to obtain their crystal structures. FIGS. 16A and 16B shows the success of one such experiment, where we observed the ligand to bind at the M-site, a site separate from the allosteric sites, the C site and the P site of hRRM1. This novel ligand-binding site establishes that we have discovered a new class of modulators of RR activity. During step 3, several cell culture experiments were conducted to assess the potency of the RR modulators in their ability to kill cancer. In one set of experiments, the modulators were tested as monotherapies. One of the ligands had a concentration at half-maximal inhibition IC$_{50}$ of approximately 200 nM, meaning it had a higher potency than gemcitabine against colon and breast cancer cell lines (FIG. 15). Moreover, in a parallel study a modulator acted synergistically with gemcitabine improving gemcitabine's therapeutic index (FIG. 15). These exciting initial results may pave the way to develop a new class of safer anticancer agents. In this project we propose to study the mechanism of action of this new class of RR modulators using a structural and biochemical approach.

TABLE 4

| Compound Number | Compound Structure | IC$_{50}$ (μM) |
|---|---|---|
| Compound 1 | 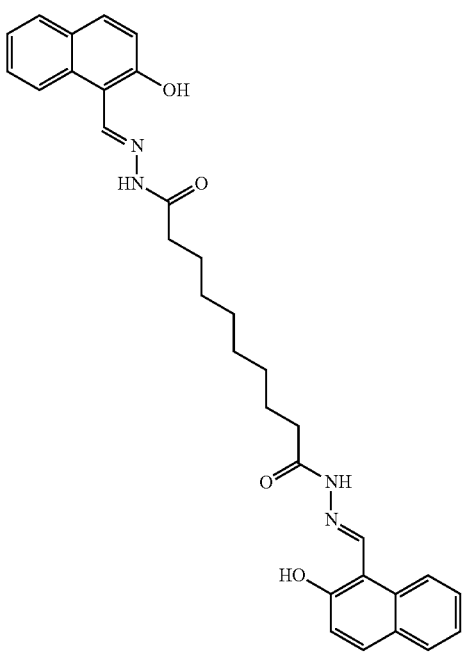 [SMILES: O=C(CCCCCCCCC(=O)N/N=C/c1c(O)ccc2ccccc12)N/N=C/c1c(O)ccc2ccccc12] | 0.6-2 |

TABLE 4-continued

| Compound Number | Compound Structure | IC$_{50}$ (µM) |
|---|---|---|
| Compound 2 | 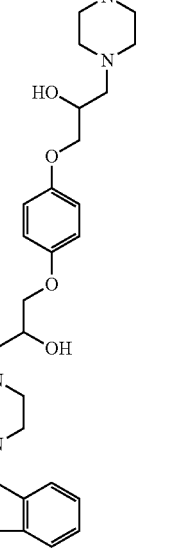 | 3-8 |
| Compound 3 | 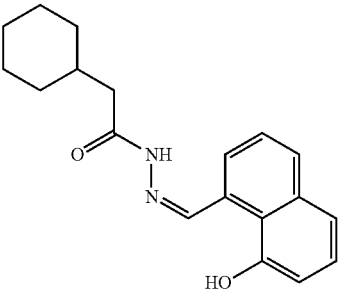 [SMILES: O=C(CC1CCCCC1)N/N=C\c1cccc2cccc(O)c12] | 0.225 |
| Compound 4 | 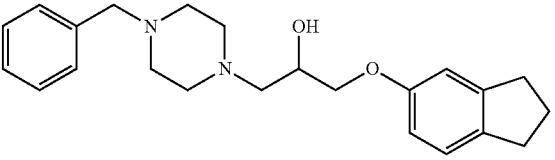 [SMILES: OC(COc1ccc2c(c1)CCC2)CN1CCN(Cc2ccccc2)CC1] | 5-10 |
| Compound 5 | 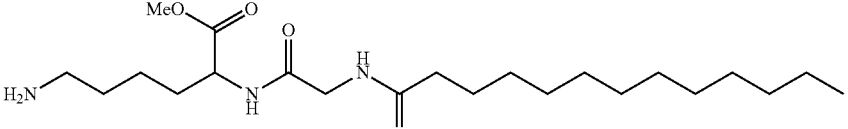 | 5-10 |
| Compound 6 | 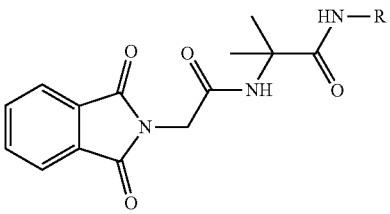 | 30 |

From the above description of the invention, those skilled in the art will perceive improvements, changes and modifications Such improvements, changes and modifications are within the skill of the art and are intended to be covered by the appended claims. All publications, patents, and patent applications cited in the present application are herein incorporated by reference in their entirety.

Having described the invention, the following is claimed:

1. A method of inhibiting ribonucleotide reductase activity in a cancer cell comprising administering to the cell an amount of a ribonucleotide reductase allosteric modulator (RRAmod), the amount being the amount effective to inhibit cancer cell growth, the RRAmod comprising a small molecule having the formula:

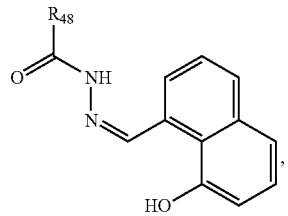

wherein $R_{46}$ is selected from the group consisting of hydrogen, substituted or unsubstituted C1-C24 alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl) substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfa, sulfonato, $C_1$-$C_{24}$ alkyisulfanyl, arylsulfanyl, $C_1$-$C_{24}$ alkylsulfinyl $C_5$-$C_{20}$ arylsulfinyl, $C_5$-$C_{20}$ arylsulfonyl, phosphono, phosphonato, phosphinato, phospho, and phosphino; or a pharmaceutically acceptable salt thereof, the cancer cell comprising a pancreatic, breast, colon or glioblastoma cancer cell.

2. The method of claim 1, wherein the RRAmod inhibiting ribonucleotide reductase activity by selectively binding at the hexamer interface of RR1.

3. The method of claim 2, the hexamer interface of RR1 comprising an epitope having an amino acid sequence corresponding to SEQ ID NO: 1.

4. The method of claim 1, wherein inhibiting ribonucleotide reductase activity comprises inhibiting ribonucleotide reductase mediated catalyzation of ribonucleotides to deoxy ribonucleotides in the cancer cell, thereby unbalancing the nucleotide pool of DNA precursor molecules required for de novo DNA synthesis.

5. The method of claim 1, wherein the RRAmod is a small molecule having the formula:

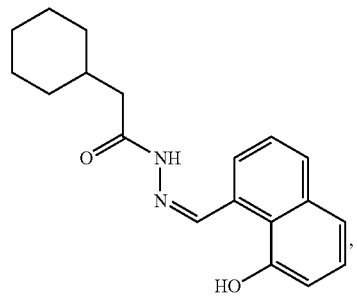 [SMILES: O=C(CC1CCCCC1)N/N=C\c1cccc2cccc(O)c12]

or pharmaceutically acceptable salts thereof.

* * * * *